US011174497B2

(12) United States Patent
Verstrepen et al.

(10) Patent No.: US 11,174,497 B2
(45) Date of Patent: Nov. 16, 2021

(54) YEAST ALLELES INVOLVED IN TOLERANCE TO HIGH ALCOHOL LEVELS

(71) Applicants: VIB VZW, Ghent (BE); KATHOLIEKE UNIVERSITEIT LEUVEN, K.U. Leuven R&D, Leuven (BE)

(72) Inventors: Kevin Verstrepen, Leuven (BE); Yudi Yang, Heverlee (BE); Veerle Saels, Herselt (BE); Karin Voordeckers, Heverlee (BE); Beatriz Herrera, Huldenberg (BE)

(73) Assignees: VIB VZW, Ghent (BE); K.U. Leuven Research & Development, Leuven (BE)

( * ) Notice: Subject to any disclaimer, the term of this patent is extended or adjusted under 35 U.S.C. 154(b) by 722 days.

(21) Appl. No.: 15/754,524

(22) PCT Filed: Sep. 2, 2016

(86) PCT No.: PCT/EP2016/070732

§ 371 (c)(1),
(2) Date: Feb. 22, 2018

(87) PCT Pub. No.: WO2017/037241

PCT Pub. Date: Mar. 9, 2017

(65) Prior Publication Data

US 2018/0312878 A1 Nov. 1, 2018

(30) Foreign Application Priority Data

Sep. 3, 2015 (EP) .................................... 15183670

(51) Int. Cl.

*C12P 7/06* (2006.01)
*C07K 14/395* (2006.01)
*C12N 15/81* (2006.01)

(52) U.S. Cl.

CPC .............. *C12P 7/06* (2013.01); *C07K 14/395* (2013.01); *C12N 15/81* (2013.01); *Y02E 50/10* (2013.01)

(58) Field of Classification Search

CPC ......... C12P 7/06; C12N 15/81; C07K 14/395; Y02E 50/10

See application file for complete search history.

(56) References Cited

U.S. PATENT DOCUMENTS

2012/0064591 A1 3/2012 Gasch et al.

FOREIGN PATENT DOCUMENTS

WO 2014170330 A2 10/2014
WO 2017037241 A1 3/2017

OTHER PUBLICATIONS

Zheng et al., Construction of Novel *Saccharomyces cerevisiae* Strains for Bioethanol Active Dry Yeast (ADY) Production, PLOS ONE, vol. 8, Issue: 2 (Year: 2013).*

Arahami-Moyal et al., Turbidostat culture of *Saccharomyces cerevisiae* W303-1A under selective pressure elicited by ethanol selects for mutations in SSD1 and UTH1, FEMS Yeast Research, Apr. 23, 2012, pp. 521-533, vol. 12, No. 5.

Claesen et al., A hidden Markov-model for gene mapping based on whole-genome next generation sequencing data, Statistical Applications in Genetics and Molecular Biology, Dec. 5, 2014, pp. 21-34, vol. 14, No. 1.

Duitama et al., Improved linkage analysis of Quantitative Trait Loci usig bulk segregants unveils a novel determinant of high ethanol tolerance in yeast, BMC Genomics, Mar. 19, 2014, pp. 207, vol. 15, No. 1, Biomed Central Ltd, London, UK.

Estruch et al., A genetic screen in *Saccharomyces cerevisiae* identifies new genes that interact with mex67-5, a temperature-sensitive allele of the gene encoding the mRNA export receptor, Molecular Genetics and Genomics, Nov. 26, 2008, pp. 125-134, vol. 281, No. 1, Springer, Berlin, DE.

Izawa, Ethanol Stress Response in the mRNA Flux of *Saccharomyces cerevisiae*, Bioscience Biotechnology Biochemistry, Jan. 7, 2010, pp. 7-12, vol. 74, No. 1.

Pais et al., Comparative Polygenic Analysis of Maximal Ethanol Accumulation Capacity and Tolerance to High Ethanol Levels of Cell Proliferation in Yeast, PLOS Genetics, Jun. 6, 2013, vol. 9, No. 6.

PCT International Search Report, PCT/EP2016/070732, dated Feb. 1, 2017.

PCT International Written Opinion, PCT/EP2016/070732, dated Feb. 1, 2017.

Swinnen et al., Identification of novel causative genes determining the complex trait of high ethanol tolerance in yeast using pooled-segregant whole-genome sequence analysis, Genome Research, Mar. 7, 2012, pp. 975-984, vol. 22, No. 5, Cold Spring Harbor Laboratory Press, United States.

Voordeckers et al., Adaptation to High Ethanol Reveals Complex Evolutionary Pathways, PLOS Genetics, Nov. 6, 2015, pp. e1005635, vol. 11, No. 11.

Yoshida et al., Hsp16p Is Required for Thermotolerance in Nuclear mRNA Export in Fission Yeast *Schizosaccharomyces pombe*, Cell Structure and Function, Apr. 19, 2005, vol. 29, No. 5, 6.

Zheng et al., Construction of Novel *Saccharomyces cerevisiae* Strains for Bioethanol Active Dry Yeast (ADY) Production, PLOS ONE, Dec. 23, 2013, pp. e85022, vol. 8, No. 12.

* cited by examiner

*Primary Examiner* — Channing S Mahatan
(74) *Attorney, Agent, or Firm* — Patent Law Works, LLP

(57) ABSTRACT

The present application relates to the field of yeast and, specifically, to the identification of yeast alleles that are involved in maximal alcohol accumulation and/or in tolerance to high alcohol levels. Preferably, the alcohol is ethanol. The identified alleles can be combined or stacked with each other to construe and/or select high alcohol tolerant yeasts, most notably *Saccharomyces* species.

6 Claims, 10 Drawing Sheets
(10 of 10 Drawing Sheet(s) Filed in Color)

Specification includes a Sequence Listing.

| | diff | lwr | upr | p adj |
|---|---|---|---|---|
| hem13-mut-ER | -0.46 | -1.205767955 | 0.285767955 | 0.662503348 |
| hst4-mut-ER | 0.66 | -0.085767955 | 1.405767955 | 0.134227249 |
| mex67-mut-ER | 0.7275 | -0.018267955 | 1.473267955 | 0.062416713 |
| pca1-mut-ER | 0.5475 | -0.198267955 | 1.293267955 | 0.380630658 |
| prt1-mut-ER | 0.565 | -0.180767955 | 1.310767955 | 0.331004377 |
| | | | | |
| vps70-mut30-ER | 0.5975 | -0.581662672 | 1.776662672 | 0.885484154 |
| ybl059w-mut-ER | 0.2875 | -0.458267955 | 1.033267955 | 0.987012267 |
| hem13-mut-hem13-ct | -0.76 | -1.505767955 | -0.014232045 | 0.041903951 |
| hst4-mut-hst4-ct | 0.4825 | -0.263267955 | 1.228267955 | 0.588455105 |
| mex67-mut-mex67-ct | 0.7975 | 0.051732045 | 1.543267955 | 0.025922402 |
| pca1-mut-pca1-ct | 0.255 | -0.490767955 | 1.000767955 | 0.995973303 |
| prt1-mut-prt1-ct | 0.2925 | -0.453267955 | 1.038267955 | 0.984783897 |
| | | | | |
| vps70-mut30-vps70-ct | 0.3825 | -0.796662672 | 1.561662672 | 0.997676717 |
| ybl059w-mut-ybl059w-ct | 0.2975 | -0.448267955 | 1.043267955 | 0.982266714 |

YEAST ALLELES INVOLVED IN TOLERANCE TO HIGH ALCOHOL LEVELS

CROSS-REFERENCE TO RELATED APPLICATIONS

This application is a national phase entry under 35 U.S.C. § 371 of International Patent Application PCT/EP2016/070732, filed Sep. 2, 2016, designating the United States of America and published in English as International Patent Publication WO 2017/037241 A1 on Mar. 9, 2017, which claims the benefit under Article 8 of the Patent Cooperation Treaty to European Patent Application Serial No. 15183670.7, filed Sep. 3, 2015.

TECHNICAL FIELD

The present application relates to the field of yeast and, specifically, to the identification of yeast alleles that are involved in maximal alcohol accumulation and/or intolerance to high alcohol levels. Preferably, the alcohol is ethanol. The identified alleles can be combined or stacked with each other to construe and/or select high alcohol-tolerant yeasts, most notably *Saccharomyces* species.

STATEMENT ACCORDING TO 37 C.F.R. § 1.821(c) or (e)—SEQUENCE LISTING SUBMITTED AS ASCII TEXT FILE

Pursuant to 37 C.F.R. § 1.821(c) or (e), a file containing an ASCII text version of the Sequence Listing has been submitted concomitant with this application, titled V525_ST25.txt, created on Feb. 22, 2018 and having a size of 18034 bytes, the contents of which are hereby incorporated by reference.

BACKGROUND

The capacity to produce high levels of alcohol is a very rare characteristic in nature. It is most prominent in the yeast *Saccharomyces cerevisiae*, which is able to accumulate in the absence of cell proliferation, ethanol concentrations in the medium of more than 17% (V/V), a level that kills virtually all competing microorganisms. As a result, this property allows this yeast to outcompete all other microorganisms in environments rich enough in sugar to sustain the production of such high ethanol levels (Casey and Ingledew, 1986; D'Amore and Stewart, 1987). Very few other microorganisms, e.g., the yeast *Dekkera bruxellensis*, have independently evolved a similar but less pronounced ethanol tolerance compared to *S. cerevisiae* (Rozpedowska et al., 2011). The capacity to accumulate high ethanol levels lies at the basis of the production of nearly all alcoholic beverages as well as bioethanol in industrial fermentations by the yeast *S. cerevisiae*. Originally, all alcoholic beverages were produced with spontaneous fermentations in which *S. cerevisiae* gradually increases in abundance, in parallel with the increase in the ethanol level, to finally dominate the fermentation at the end. The ability to survive and proliferate in high levels of ethanol is an ecologically important and industrially relevant trait of yeast cells. The ethanol produced by yeast cells slows down growth of competing microbes, but at higher concentrations, it causes stress for the yeast cells themselves. Different yeast strains show significant differences in their ability to grow in the presence of ethanol, with the more ethanol-tolerant ones likely having a fitness advantage over non-tolerant strains.[1-3] Moreover, ethanol tolerance is a key trait of industrial yeasts that often encounter very high ethanol concentrations, for example, during beer and wine making and industrial bio-ethanol production.

The genetic basis of yeast alcohol tolerance, particularly ethanol tolerance, has attracted much attention but, until recently, nearly all research was performed with laboratory yeast strains, which display much lower alcohol tolerance than the natural and industrial yeast strains. This research has pointed to properties like membrane lipid composition, chaperone protein expression and trehalose content, as major requirements for ethanol tolerance of laboratory strains (D'Amore and Stewart, 1987; Ding et al., 2009), but the role played by these factors in other genetic backgrounds and in establishing tolerance to very high ethanol levels has remained unknown. Different experimental approaches have been used, including screening of (deletion) mutants for increased ethanol tolerance, transcriptome analysis of ethanol-stressed cells and QTL analyses aimed at identifying mutations that cause differences in ethanol tolerance between different yeast strains.[4-10] A polygenic analysis of the high ethanol tolerance of a Brazilian bioethanol production strain VR1 revealed the involvement of several genes previously never connected to ethanol tolerance and did not identify genes affecting properties classically considered to be required for ethanol tolerance in lab strains (Swinnen et al., 2012a). Together, these studies have linked multiple different genetic loci to ethanol tolerance and identified hundreds of genes involved in a multitude of cellular processes.[11-14]

A shortcoming of most previous studies is the assessment of alcohol tolerance solely by measuring growth on nutrient plates in the presence of increasing alcohol levels (D'Amore and Stewart, 1987; Ding et al., 2009). This is a convenient assay, which allows hundreds of strains or segregants to be phenotyped simultaneously with little work and manpower. However, a more physiologically and ecologically relevant parameter of alcohol tolerance in *S. cerevisiae* is its capacity to accumulate by fermentation high alcohol levels in the absence of cell proliferation. This generally happens in an environment with a large excess of sugar compared to other essential nutrients. As a result, a large part of the alcohol in a typical, natural or industrial, yeast fermentation is produced with stationary phase cells in the absence of any cell proliferation. The alcohol tolerance of the yeast under such conditions determines its maximal alcohol accumulation capacity, a specific property of high ecological and industrial importance. In industrial fermentations, a higher maximal alcohol accumulation capacity allows a better attenuation of the residual sugar and, therefore, results in a higher yield. A higher final alcohol titer reduces the distillation costs and also lowers the liquid volumes in the factory, which has multiple beneficial effects on costs of heating, cooling, pumping and transport of liquid residue. It also lowers microbial contamination and the higher alcohol tolerance of the yeast generally also enhances the rate of fermentation, especially in the later stages of the fermentation process. Maximal alcohol accumulation capacity can only be determined in individual yeast fermentations, which are much more laborious to perform than growth tests on plates. In static industrial fermentations, maintenance of the yeast in suspension is due to the strong $CO_2$ bubbling and this can only be mimicked in lab scale with a sufficient amount of cells in a sufficiently large volume.

While it becomes increasingly clear that ethanol is a complex stress that acts on several different processes including increasing fluidity and permeability of cellular membranes, changing activity and solubility of membrane-bound and cytosolic proteins and interfering with the proton motive force (for review, see references 15-17 herein, the exact molecular mechanisms and genetic architecture underlying ethanol tolerance are still largely unknown.

Experimental evolution to study adaptation to increased ethanol levels could provide more insight into the molecular mechanisms underlying ethanol tolerance since such experiments could reveal different mutational paths that make a sensitive strain more tolerant. Only a handful of studies have looked at adaptation to ethanol in originally non-ethanol-tolerant microbes exposed to gradually increasing levels of ethanol.[6, 18-22] These have mostly focused on the physiological adaptations found in the evolved cells and have not performed an extensive analysis of the mechanisms and genetic changes underlying this adaptation. Hence, a comprehensive analysis of the type and number of mutations a non-ethanol-tolerant strain can (or needs to) acquire to become more ethanol tolerant is still lacking. Experimental evolution has proven to be a valuable tool to investigate the different mechanisms and pathways important for cells to adapt to specific selective conditions. Seminal papers have increased the understanding of the molecular basis of adaptation to specific stresses, such as heat stress, nutrient limitation and antibiotic treatment.[32-28] Recent advances in DNA sequencing technologies allow affordable and fast sequencing of complete genomes of clones and populations. While sequencing clones yields information on individual lineages within the experiment, population data provides information on the heterogeneity of adaptation. Additionally, sequencing samples isolated at different time points during the evolution experiment makes it possible to capture evolution in action. This has provided valuable information on the rate and types of mutations underlying adaptation, the genetic basis of "novel" phenotypes and the existence of parallel pathways to establish comparable phenotypic outcomes.[29-32] For example, a common strategy observed in populations evolving under nutrient limitation is the amplification of genetic regions encoding transporters responsible for the uptake of the limiting nutrient.[24-33] Other studies using multiple replicate populations have discovered a high degree of parallelism in the adaptive solutions found by different populations. Clonal interference, the competition between lineages carrying different beneficial mutations, is another commonly observed phenomenon in evolution of asexually propagating populations that can increase complexity of mutational dynamics as well as impede the spread of beneficial mutations in a population.[32, 34, 35] To unravel the molecular mechanisms of adaptation to a specific condition, most studies have used isogenic replicate populations, with all cells having the same initial genome size. Genome size can significantly change during evolution; with both small-scale changes (chromosomal 108 deletions and amplifications) and large-scale changes (increase or decrease in ploidy). Moreover, ploidy shifts have been reported in the evolutionary history of many organisms, including *Saccharomyces cerevisiae* and as a response to selective pressure.[36-38] Conversely, genome size has also been reported to affect evolution rate: polyploidy has been shown to increase adaptability.[39, 40] Multiplying the amount of DNA increases the genetic material available for evolution to tinker with and can alter gene expression.[41-43] These polyploid genomes can be unstable, resulting in loss of chromosomes and, thus, aneuploid cells.[44-46] Although studies have looked at adaptation of lineages of different ploidy, none have followed in detail the mutational dynamics in these evolving populations over time.[36, 47-49]

It would be advantageous to identify novel pathways and alleles that contribute to alcohol tolerance and are relevant in industrial yeast strains as well, to further increase yield of alcohol fermentations with such strains. Indeed, even a slight increase in alcohol tolerance or alcohol accumulation capacity would have huge economic benefits.

BRIEF SUMMARY

Experimental evolution of isogenic yeast populations of different initial ploidy was used to study adaptation to increasing levels of ethanol. Evolved lineages showed a significant increase in ethanol tolerance compared to ancestral strains. High coverage whole-genome sequencing of more than 30 evolved populations and over 100 adapted clones isolated throughout a two-year evolution experiment revealed how a complex interplay of different evolutionary mechanisms led to higher tolerance, including de novo single nucleotide mutations, extensive copy number variation and ploidy changes. Although the specific mutations differ between different evolved lineages, application of a novel computational pipeline to identify target pathways reveals shared themes at the level of functional modules. Moreover, by combining an allelic replacement approach with high-throughput fitness measurements, several SNPs that arose in the adapted cells previously not implicated in ethanol tolerance were identified and that significantly increased ethanol tolerance when introduced into a non-tolerant background. Taken together, the results show how, in contrast to adaptation to some other stresses, adaptation to a complex and severe stress involves an interplay of different evolutionary mechanisms. In addition, the study highlights the potential of experimental evolution to identify mutations that are of industrial importance.

Provided are alleles that increase alcohol tolerance and/or alcohol accumulation in yeast. Most particularly, the alcohol is ethanol. Most particularly, the yeast is a *Saccharomyces* species. Increase in alcohol tolerance is an economically relevant property and, as a non-limiting example, an increase in alcohol tolerance and/or accumulation may be favorable for bio-ethanol production. The increase in alcohol tolerance and/or accumulation may result in a higher speed of fermentation (i.e., less time needed to reach a particular percentage of alcohol) and/or a higher final ethanol titer.

According to specific embodiments, such alleles are selected from an MEX67 allele, a PCA1 allele, a PRT1 allele, a YBL059W allele, an HEM13 allele, an HST4 allele, and a VPS70 allele. The alleles can also be in intergenic regions. According to these embodiments, the alleles are typically selected from the intergenic region of Chromosome IV (particularly around or at position 1489310) and the intergenic region of Chromosome XII (particularly around or at position 747403).

Particularly envisaged alleles are selected from the group consisting of an MEX67 allele with a G456A mutation, PCA1 with a C1583T mutation, PRT1 with an A1384G mutation, YBL059W with a G479T mutation, HEM13 with a G700C mutation, HST4 with a G262C mutation, VPS70 with a C595A mutation, the intergenic region of Chromosome W with an A>T substitution at position 1489310, and the intergenic region of Chromosome XII with aC>T substitution at position 747403. It is particularly envisaged that the wild-type alleles mentioned are selected from MEX67 as shown in SEQ ID NO: 1, PCA1 as shown in SEQ ID NO: 2, PRT1 as shown in SEQ ID NO: 3, YBL059W as shown in SEQ ID NO: 4, HEM13 as shown in SEQ ID NO: 5, HST4 as shown in SEQ ID NO: 6, and VPS70 as shown in SEQ ID NO: 7. Thus, it is particularly envisaged that the allele is selected from the group consisting of SEQ ID NO: 1 with a G456A mutation, SEQ ID NO: 2 with a C1583T mutation, SEQ ID NO: 3 with an A1384G mutation, SEQ ID NO: 4 with a G479T mutation, SEQ ID NO: 5 with a G700C mutation, SEQ ID NO: 6 with a G262C mutation, or SEQ ID NO: 7 with a C595A mutation.

The alleles can be used to increase alcohol tolerance and/or alcohol accumulation in yeast, either alone or in combination. The latter provides additive or even synergistic effects. Any permutation/combination of the nine alleles can be used to increase alcohol tolerance and/or alcohol accumulation, and this is explicitly envisaged herein. Any combination of these alleles (including single alleles) may also be combined with known mutations or alleles that increase alcohol tolerance and/or alcohol accumulation. This is particularly the case when the alleles are to be used in industrial yeast strains adapted to have high alcohol tolerance.

Particularly envisaged combinations are those with the MEX67 allele. According to these embodiments, an MEX67 allele is provided to increase alcohol tolerance and/or alcohol accumulation in yeast. This MEX67 allele may be combined with other alcohol tolerance and/or accumulation-modulating alleles. This may be known as alcohol tolerance alleles. It is also explicitly foreseen that the MEX67 allele may be incorporated in an industrial yeast strain adapted to have high alcohol tolerance (and that thus already has a combination of known alcohol tolerance alleles). However, it is also explicitly envisaged that the MEX67 allele is further combined with the new alcohol tolerance and/or accumulation-modulating alleles reported herein. According to these embodiments, the use of a MEX67 allele is provided, wherein the MEX67 allele is combined with other alcohol tolerance and/or accumulation-modulating alleles. Particularly, the other alcohol tolerance and/or accumulation-modulating alleles are selected from the group consisting of PCA1, PRT1, YBL059W, HEM13, HST4, and VPS70. According to alternative embodiments, they may also be selected from the intergenic region of Chromosome IV (particularly around or at position 1489310) and the intergenic region of Chromosome XII (particularly around or at position 747403). According to specific embodiments, the MEX67 allele has a G456A mutation. According to further specific embodiments, the other alcohol tolerance and/or accumulation-modulating alleles are selected from the group consisting of PCA1 with a C1583T mutation, PRT1 with an A1384G mutation, YBL059W with a G479T mutation, HEM13 with a G700C mutation, HST4 with a G262C mutation, VPS70 with a C595A mutation, the intergenic region of Chromosome IV with an A>T substitution at position 1489310, and the intergenic region of Chromosome XII with a C>T substitution at position 747403.

Albeit that the combinations with the MEX67 alleles are particularly envisaged, the above applies mutatis mutandis to the other alleles described herein (e.g., the PCA1, PRT1, YBL059W, . . . alleles).

The alleles described herein have not before been linked to increased alcohol tolerance or accumulation. This is also true for the genes and intergenic regions, with exception of VPS70. For VPS70, another allele has recently been shown to also modulate alcohol tolerance (WO2014/170330). Thus, according to particular embodiments, VPS70 is excluded from the envisaged combinations. According to alternative embodiments, when a VPS70 allele is used to increase alcohol tolerance and/or accumulation, it is the VPS70 allele with a C595A mutation.

According to a further aspect, the alleles provided herein, particularly the MEX67 allele, are used for selecting a yeast strain with higher alcohol accumulation and/or resistance. Particularly, the yeast is a *Saccharomyces* spp. Particularly, the alcohol is ethanol.

The selection of the strain can be carried out with every method known to the person skilled in the art. As a non-limiting example, strains may be selected on the basis of an identification of the allele by PCR or hybridization. The selection may be combined by a selection for other alleles, known to be involved in alcohol accumulation and/or alcohol tolerance, such as, but not limited to, specific alleles of ADE1, VPS70, MKT1, APJ1, SWS2, or KIN3. The selection may be carried out simultaneously or consecutively. In the case of a consecutive selection, the sequence of the selection is not important, i.e., the selection using MEX67 may be carried out before or after the other selection rounds.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION

Definitions

Figure 1:
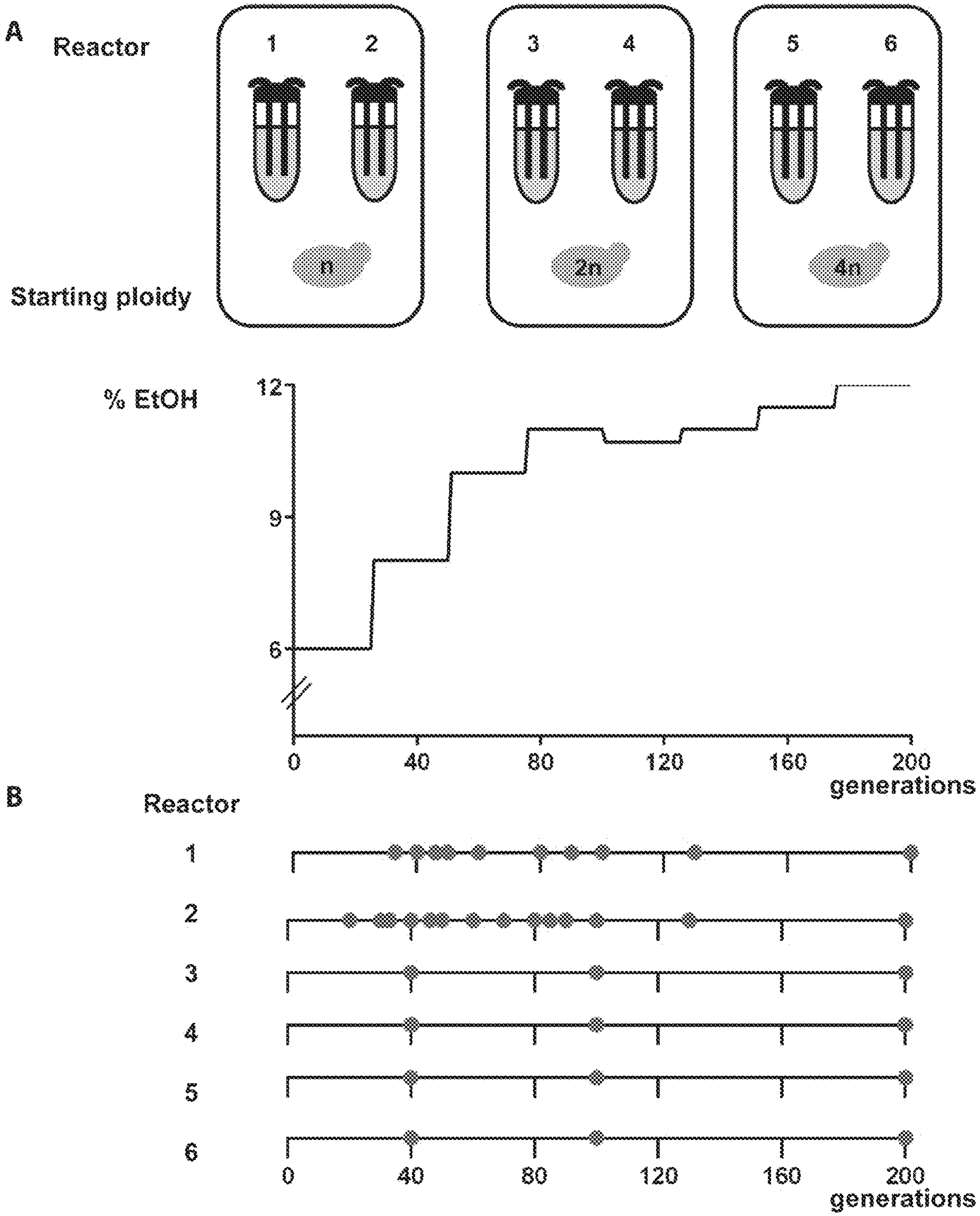
FIG. 1: Experimental setup. (Panel A) Experimental evolution of prototrophic, isogenic populations of different ploidy (haploid (VK111), diploid (VK145) and tetraploid (VK202)) for increased ethanol tolerance was performed in a turbidostat. Every 25 generations, the ethanol concentration in the media was increased in a stepwise manner (starting at 6% (v/v) and reaching 12% at 200 generations). Increasing the ethanol concentration from 10% to 11% dramatically reduced growth rate of evolving cells. Therefore, instead of increasing ethanol levels, the ethanol level was first reduced to 10.7% after 100 generations. (Panel B) Red circles represent sampling points (indicated as number of generations) for which whole-genome sequencing was performed. For each circle, heterogeneous populations as well as three evolved, ethanol-tolerant clones were sequenced. Sequencing of the population sample of reactor 4 at 200 generations failed, so this data is omitted from the specification. For generation 80 of reactor 1, only population data is available.

This disclosure will be described with respect to particular embodiments and with reference to certain drawings but the disclosure is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term “comprising” is used in the present description and claims, it does not exclude other elements or steps. Where an indefinite or definite article is used when referring to a singular noun, e.g., “a,” “an,” or “the,” this includes a plural of that noun unless something else is specifically stated.

Furthermore, the terms “first,” “second,” “third,” and the like in the description and in the claims, are used for distinguishing between similar elements and not necessarily for describing a sequential or chronological order. It is to be understood that the terms so used are interchangeable under appropriate circumstances and that the embodiments of the disclosure described herein are capable of operation in other sequences than described or illustrated herein.

The following terms or definitions are provided solely to aid in the understanding of the disclosure. Unless specifically defined herein, all terms used herein have the same meaning as they would to one skilled in the art of the present disclosure. Practitioners are particularly directed to Sambrook et al., *Molecular Cloning: A Laboratory Manual,* 2$^{nd}$ ed., Cold Spring Harbor Press, Plainsview, N.Y. (1989); and Ausubel et al., *Current Protocols in Molecular Biology* (Supplement 47), John Wiley & Sons, New York (1999), for definitions and terms of the art. The definitions provided herein should not be construed to have a scope less than understood by a person of ordinary skill in the art.

An “allele,” as used herein, is a specific form of the gene that is carrying SNPs or other mutations, either in the coding (reading frame) or the non-coding (promoter region, or 5' or 3' non-translated end) part of the gene, wherein the mutations distinguish the specific form from other forms of the gene.

“Gene,” as used herein, includes both the promoter and terminator region of the gene as well as the coding sequence. It refers both to the genomic sequence (including possible introns) as well as to the cDNA derived from the spliced messenger, operably linked to a promoter sequence.

“Coding sequence” is a nucleotide sequence that is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to, mRNA, cDNA, recombinant nucleotide sequences or genomic DNA, while introns may be present as well under certain circumstances.

"Promoter region" of a gene as used herein refers to a functional DNA sequence unit that, when operably linked to a coding sequence and possibly a terminator sequence, as well as possibly placed in the appropriate inducing conditions, is sufficient to promote transcription of the coding sequence.

"Nucleotide sequence," "DNA sequence," or "nucleic acid molecule(s)" as used herein refers to a polymeric form of nucleotides of any length, either ribonucleotides or deoxyribonucleotides. This term refers only to the primary structure of the molecule. Thus, this term includes double- and single-stranded DNA and RNA. It also includes known types of modifications, for example, methylation, "caps" substitution of one or more of the naturally occurring nucleotides with an analog.

"Modulation of alcohol accumulation and/or tolerance," as used herein, means an increase or a decrease of the alcohol concentration, produced by the yeast carrying the specific allele, as compared with the alcohol concentration produced under identical conditions by a yeast that is genetically identical, apart from the specific allele(s).

"Alcohol," as used herein, can be any kind of alcohol including, but not limited to, methanol, ethanol, n- and isopropanol, and n- and isobutanol. Indeed, several publications indicate that the tolerance to ethanol and other alkanols is determined by the same mechanisms (Carlsen et al., 1991; Casal et al., 1998).

The causes and mechanisms underlying evolutionary adaptation are key issues in biology. However, the mechanisms underlying evolutionary adaptation to complex and severe stress factors (e.g., broadly acting toxins or extreme niches that require immediate, complex adaptive changes) remain understudied. Here, how yeast populations adapt to gradually increasing ethanol levels is studied—a broad-acting, ecologically and industrially relevant complex stress that is still poorly understood. The results reveal how over a two-year evolution period, several evolutionary mechanisms, including mutator phenotypes, changes in ploidy, and complex clonal interference, result in adapted populations capable of surviving in medium containing up to 12% ethanol. In addition, several previously unknown adaptive mutations that increase ethanol resistance are reported, which may open new routes to increase the efficiency of industrial fermentations. Specifically, six initially isogenic yeast populations of different ploidy were exposed to increasing levels of ethanol. High-coverage, whole-genome sequencing of more than 30 populations and 100 clones isolated throughout this two-year evolution experiment were combined with a novel computational pipeline to reveal the mutational dynamics, molecular mechanisms and networks underlying increased ethanol tolerance of the evolved lineages. High-throughput fitness measurements allowed characterization of the phenotypic effect of identified mutations in different environments. The results suggest that adaptation to high ethanol is complex and can be reached through different mutational pathways. It was found that adaptation to high ethanol levels involves the appearance of mutator phenotypes and evolving populations showing strong clonal interference. Evolved cells display extensive variation in genome size, with initially haploid and tetraploid populations showing quick convergence to a diploid state. The results are the first to attribute a significant fitness advantage of a diploid cell over an isogenic haploid cell under selective conditions. In addition, evolved clones repeatedly gained extra copies of the same chromosomes. By combining an allelic replacement approach with high-throughput fitness measurements, several mutations previously not implicated in ethanol tolerance were identified that significantly increased ethanol tolerance when introduced into a non-tolerant background. Together, the study yields a detailed view of the molecular evolutionary processes and genetic changes underlying long-term adaptation to a severe and complex stress, and highlights the potential of experimental evolution to identify mutations that are of industrial importance. The methods developed and insights gained serve as a model for adaptation to a complex and lethal stress. Moreover, specific adaptive SNPs can be used to guide engineering strategies aimed at obtaining superior biofuel yeasts. Last but not least, the experimental setup is also interesting because it takes an atypical approach. In many experimental evolution studies, populations are exposed for a limited amount of time (typically a few months) to a defined, constant and "simple" stress (e.g., a fixed concentration of antibiotic or limiting nutrient), so that in the beginning of the experiment, cells are confronted with a very strong selection, while the selection pressure is reduced or even eliminated when cells become resistant. In the experimental set-up, ethanol levels were gradually increased over time so that cells were evolving under constant selection over a long (two-year) period. High concentrations of ethanol slow down growth and actively kill non-tolerant cells. The work disclosed herein thus combines aspects of traditional evolution studies with principles used in so-called morbidostat experiments and may, therefore, offer a realistic picture of adaptation to a complex and severe stress where a population gradually penetrates a new niche.

Provided are alleles that increase alcohol tolerance and/or alcohol accumulation in yeast. Most particularly, the alcohol is ethanol. Most particularly, the yeast is a *Saccharomyces* species.

According to specific embodiments, such alleles are selected from an MEX67 allele, a PCA1 allele, a PRT1 allele, a YBL059W allele, an HEM13 allele, an HST4 allele, and a VPS70 allele. The alleles can also be in intergenic regions. According to these embodiments, the alleles are typically selected from the intergenic region of Chromosome IV (particularly around or at position 1489310) and the intergenic region of Chromosome XII (particularly around or at position 747403).

Particularly envisaged alleles are selected from the group consisting of an MEX67 allele with a G456A mutation, PCA1 with a C1583T mutation, PRT1 with an A1384G mutation, YBL059W with a G479T mutation, HEM13 with a G700C mutation, HST4 with a G262C mutation, VPS70 with a C595A mutation, the intergenic region of Chromosome IV with an A>T substitution at position 1489310, and the intergenic region of Chromosome XII with aC>T substitution at position 747403.

The alleles can be used to increase alcohol tolerance and/or alcohol accumulation in yeast, either alone or in combination. The latter provides additive or even synergistic effects. Any permutation/combination of the nine alleles can be used to increase alcohol tolerance and/or alcohol accumulation, and this is explicitly envisaged herein. Any combination of these alleles (including single alleles) may also be combined with known mutations or alleles that increase alcohol tolerance and/or alcohol accumulation. This is particularly the case when the alleles are to be used in industrial yeast strains adapted to have high alcohol tolerance.

Particularly envisaged combinations are those with the MEX67 allele. According to these embodiments, the MEX67 allele is provided to increase alcohol tolerance and/or alcohol accumulation in yeast. This MEX67 allele may be combined with other alcohol tolerance and/or accumulation-modulating alleles. This may be known alcohol tolerance alleles. It is also explicitly foreseen that the MEX67 allele may be incorporated in an industrial yeast strain adapted to have high alcohol tolerance (and that thus already has a combination of known alcohol tolerance alleles). Non-limiting examples include ADE1, INO1, VPS70, MKT1, APJ1, SWS2, PDR1, or KIN3.

However, it is also explicitly envisaged that the MEX67 allele is further combined with the new alcohol tolerance and/or accumulation-modulating alleles reported herein. According to these embodiments, the use of an MEX67 allele is provided, wherein the MEX67 allele is combined with other alcohol tolerance and/or accumulation-modulating alleles. Particularly, the other alcohol tolerance and/or accumulation-modulating alleles are selected from the group consisting of PCA1, PRT1, YBL059W, HEM13, HST4, and VPS70. According to alternative embodiments, they may also be selected from the intergenic region of Chromosome IV (particularly around or at position 1489310) and the intergenic region of Chromosome XII (particularly around or at position 747403). According to specific embodiments, the MEX67 allele has a G456A mutation. According to further specific embodiments, the other alcohol tolerance and/or accumulation-modulating alleles are selected from the group consisting of PCA1 with a C1583T mutation, PRT1 with an A1384G mutation, YBL059W with a G479T mutation, HEM13 with a G700C mutation, HST4 with a G262C mutation, VPS70 with a C595A mutation, the intergenic region of Chromosome IV with an A>T substitution at position 1489310, and the intergenic region of Chromosome XII with a C>T substitution at position 747403.

Albeit that the combinations with the MEX67 alleles are particularly envisaged, the above applies mutatis mutandis to the other alleles described herein (e.g., the PCA1, PRT1, YBL059W, . . . alleles).

The alleles described herein have not before been linked to increased alcohol tolerance or accumulation. This is also true for the genes and intergenic regions, with exception of VPS70. For VPS70, another allele has recently been shown to also modulate alcohol tolerance. Thus, according to particular embodiments, VPS70 is excluded from the envisaged combinations. According to alternative embodiments, when a VPS70 allele is used to increase alcohol tolerance and/or accumulation, it is the VPS70 allele with a C595A mutation.

According to a further aspect, the alleles provided herein, particularly the MEX67 allele, are used for selecting a yeast strain with higher alcohol accumulation and/or resistance. Particularly, the yeast is a *Saccharomyces* spp. Particularly, the alcohol is ethanol.

In a specific embodiment, the disclosure provides a yeast strain, particularly an industrial yeast strain, particularly an industrial yeast strain of *Saccharomyces cerevisiae* comprising at least one allele selected from the group consisting of an MEX67 allele with a G456A mutation, PCA1 with a C1583T mutation, PRT1 with an A1384G mutation, YBL059W with a G479T mutation, HEM13 with a G700C mutation, HST4 with a G262C mutation, VPS70 with a C595A mutation, the intergenic region of Chromosome IV with an A>T substitution at position 1489310, and the intergenic region of Chromosome XII with a C>T substitution at position 747403.

The selection of the strain can be carried out with every method known to the person skilled in the art. As a non-limiting example, strains may be selected on the basis of an identification of the allele by PCR or hybridization. The selection may be combined by a selection for other alleles, known to be involved in alcohol accumulation and/or alcohol tolerance, such as, but not limited to, specific alleles of ADE1, VPS70, MKT1, APJ1, SWS2, or KIN3. The selection may be carried out simultaneously or consecutively. In the case of a consecutive selection, the sequence of the selection is not important, i.e., the selection using MEX67 may be carried out before or after the other selection rounds.

It is to be understood that although particular embodiments, specific configurations as well as materials and/or molecules, have been discussed herein for cells and methods according to this disclosure, various changes or modifications in form and detail may be made without departing from the scope and spirit of this disclosure. The following Examples are provided to better illustrate particular embodiments, and they should not be considered limiting the application. The application is limited only by the claims.

EXAMPLES

Example 1. Experimental Evolution to Increase Alcohol Tolerance

Introduction

In this study, experimental evolution is used to dissect the adaptive mechanisms underlying ethanol tolerance in yeast. Six isogenic *Saccharomyces cerevisiae* populations of different ploidy (haploid, diploid and tetraploid) were asexually propagated in a turbidostat over a two-year period, with ethanol levels gradually increasing during the experiment. This step-wise increase in exogenous ethanol levels resulted in a constant selective pressure for the cells. Whole-genome sequencing of evolved populations and isolated, ethanol-tolerant clones at different times during the experiment allowed painting of a detailed picture of the mutational dynamics in the different populations. Several common themes in the type of adaptations and evolutionary mechanisms emerge, with all lines showing extensive clonal interference as well as copy number variations. Additionally, the haploid and tetraploid lines showed rapid convergence toward a diploid state. Despite these common themes, multiple lineage-specific adaptations were found, with little overlap in the mutated genes between the different populations. By applying a novel computational pipeline to identify affected pathways, overlapping between the functional modules affected in the different adapted populations were revealed, with both novel and previously established pathways and genes contributing to ethanol tolerance. Importantly, introduction of specific mutated alleles present in adapted populations into the ancestral strain significantly increased its ethanol tolerance, demonstrating the adaptive nature of these mutations and the potential of using experimental evolution to unravel and improve a complex phenotype.

1.1 Evolved Cells are More Ethanol Tolerant

To study the mutational dynamics underlying increased ethanol tolerance, six prototrophic, isogenic *S. cerevisiae* strains of different ploidy (two haploid, two diploid and two tetraploid lines—with each line of the same initial ploidy started from the same preculture (VK111, VK145 and VK202, respectively) were subjected to increasing levels of ethanol. This was done by gradually increasing ethanol levels from 6% (v/v) to 12% over a two-year period in a continuous turbidostat with glucose (4% (w/v)) as a carbon source. Samples were taken at regular time intervals and subjected to whole-genome sequencing analysis. In addition to sequencing each of the six evolving populations, the genomes of three clones isolated from each of the population samples were also sequenced, resulting in a total of 34 population samples and 102 clonal samples that were sequenced. FIG. 1 depicts the experimental set-up as well as the time points (number of generations) for which whole-genome sequencing was performed.

Figure 2:
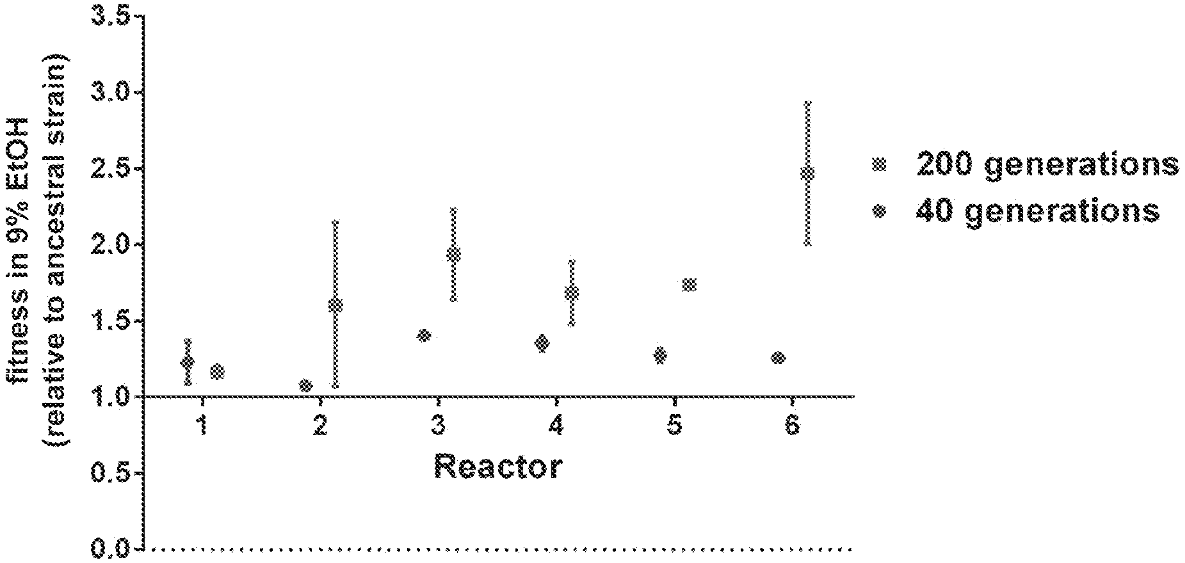
FIG. 2: Evolved populations are more ethanol tolerant. Evolved populations from different reactors show increased fitness in EtOH. Fitness was determined for population samples of each reactor after 40 generations (blue) and 200 generations (red). Fitness is expressed relative to the ancestral strain of each reactor (haploid for reactor 1-2; diploid for reactor 3-4; and tetraploid for reactor 5-6). Data represent the average of three independent measurements; error bars represent standard deviation.

The relative fitness of the evolved populations was determined, isolated at 40 and 200 generations, and generally observed increases in fitness in high (9% v/v) EtOH (FIG. 2 and Materials and Methods). In general, clones taken from the same population at the same time point had similar fitness; with some notable exceptions suggesting considerable heterogeneity within populations (data not shown). These fitness measurements were performed in 9% ethanol because the ancestral reference strains did not grow at higher ethanol levels. It is important to note that the actual increase in fitness of the evolved strains in higher ethanol levels (above 9% (v/v)) is much larger than what can be appreciated from FIG. 2. Spotting of the evolved lineages on agar plates with increasing levels of ethanol indicates that these adapted strains can grow on concentrations up to 11% (v/v) EtOH, with the control ancestral strains showing almost no growth under these conditions (i.e., an infinite increase in fitness compared to the ancestral strain) (data not shown).

Figure 3:
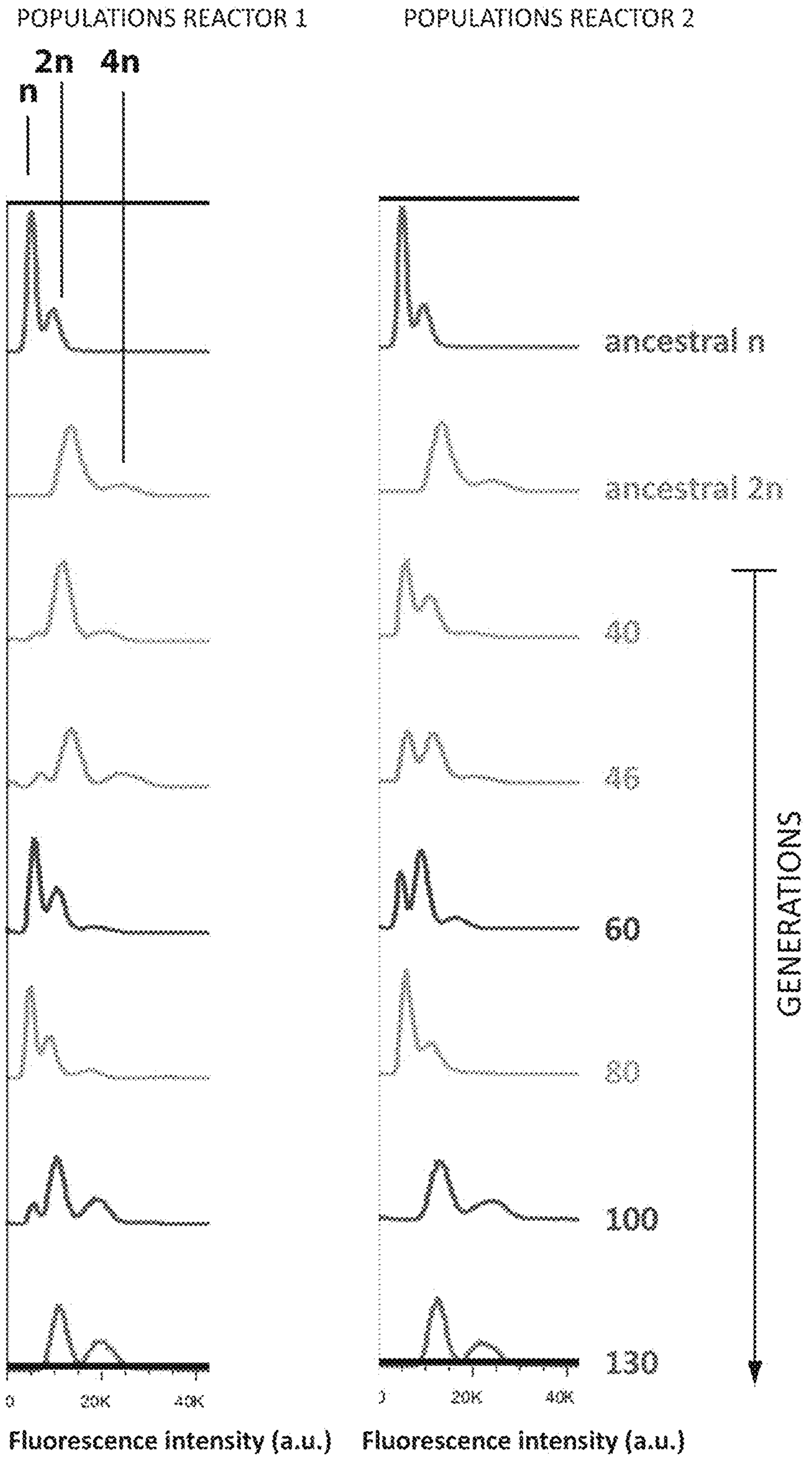
FIG. 3: Haploid lineages diploidized during adaptation to EtOH. Flow cytometry analysis of DNA content (stained by propidium iodide) of evolved populations, compared to ancestral haploid (red) and diploid (blue). For the clonal ancestral samples, two peaks are observed, corresponding to the G1 and G2 phase of the cell cycle. Evolved populations sometimes display three peaks, indicative of both haploid and diploid subpopulations.

1.2 Diploidization of Haploid Cells is a Fast Way of Increasing Ethanol Tolerance Propidium iodide staining and flow cytometry analysis of evolved populations showed that diploid cells appeared relatively quickly in the originally haploid populations (FIG. 3). This was observed independently in both reactors started from the same isogenic haploid population. In both reactors, diploid cells have taken over the entire population by 130 generations. These diploid variants are still of mating type a, the same as the initial haploid ancestral strain, indicating that they did not arise through mating type switching and subsequent mating. Our results indicate that the diploids in our turbidostat are likely the result of failed cytokinesis. The relatively rapid evolutionary sweep of the new diploid variants points to a significant selective advantage. Competition experiments confirmed that the fitness of a diploid cell is indeed significantly higher than that of an isogenic haploid strain in 9% EtOH (p=0.0063; unpaired t-test), whereas there is no significant fitness difference in the absence of ethanol (p=0.469; unpaired t-test; data not shown). Interestingly, the tetraploid starting populations also converged to a diploid state relatively fast during the evolution experiment. The parallel diploidization observed in two reactors with haploid ancestral cells and two reactors with tetraploid ancestral cells might suggest that becoming diploid is one of the main and/or one of the more easily accessible routes leading to increased ethanol tolerance.

Whole-Genome Sequencing of Evolved Populations and Clones Reveals a Complex Pattern of Adaptation To identify the mutational pathways during adaptation to ethanol, whole-genome sequencing of populations of evolving cells was performed throughout the two-year experiment. Each population sample was sequenced to 500-fold coverage on average, and this for multiple time points (34 samples for all reactors combined; see FIG. 1). In addition to this whole-population sequencing strategy, the genomes of three adapted clones were also sequenced for each time point to 80-fold coverage on average, resulting in 102 clonal samples sequenced in total. Details on the sequencing and analysis pipelines can be found in Materials and Methods.

Figure 4:
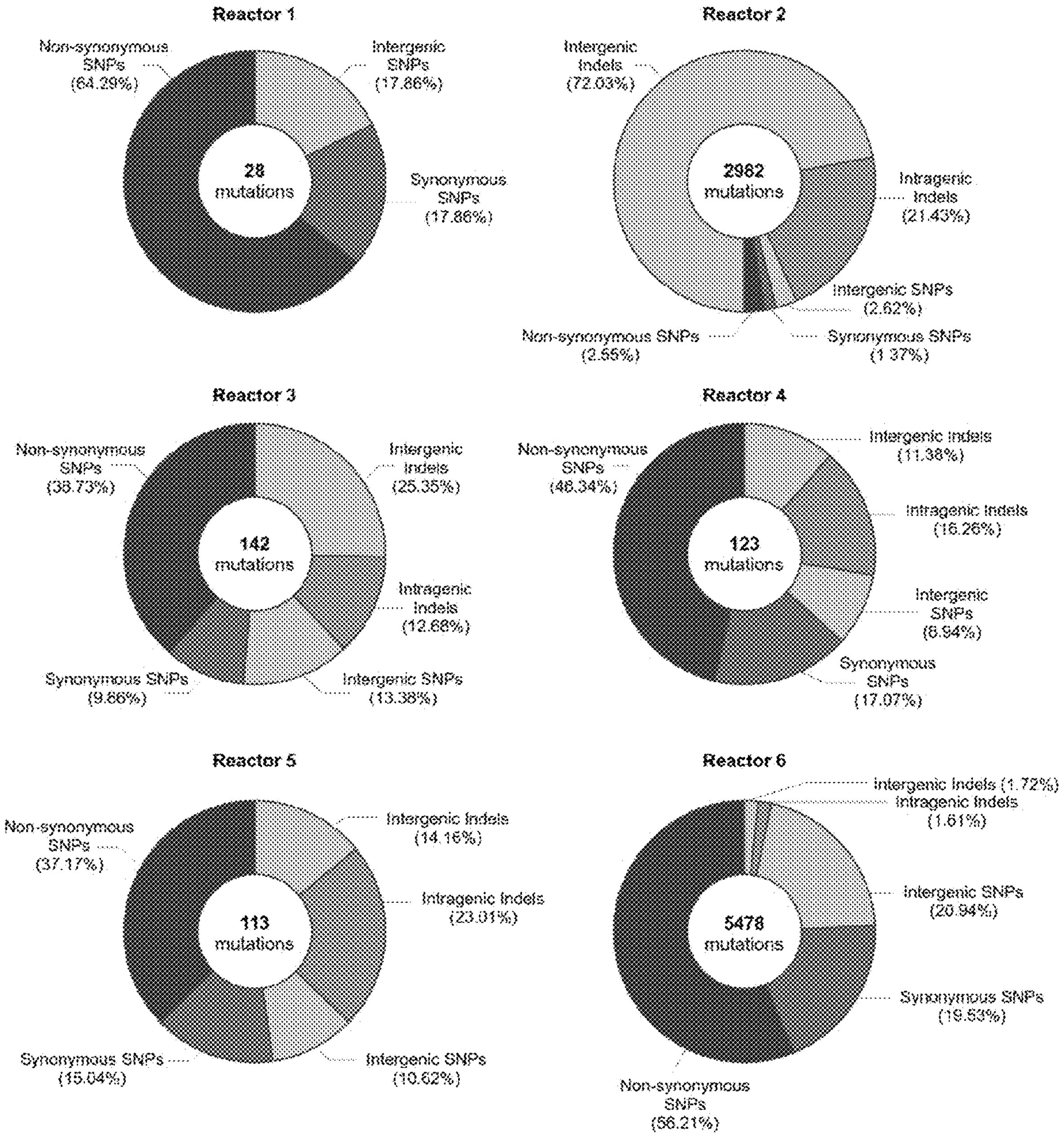
FIG. 4: Mutations present in evolved clones isolated from all reactors at 200 generations. Circle diagrams depict the number and types of mutations identified in evolved clones at 200 generations of reactor 1, reactor 2, reactor 3, reactor 4, reactor 5 and reactor 6.
Figure 5:
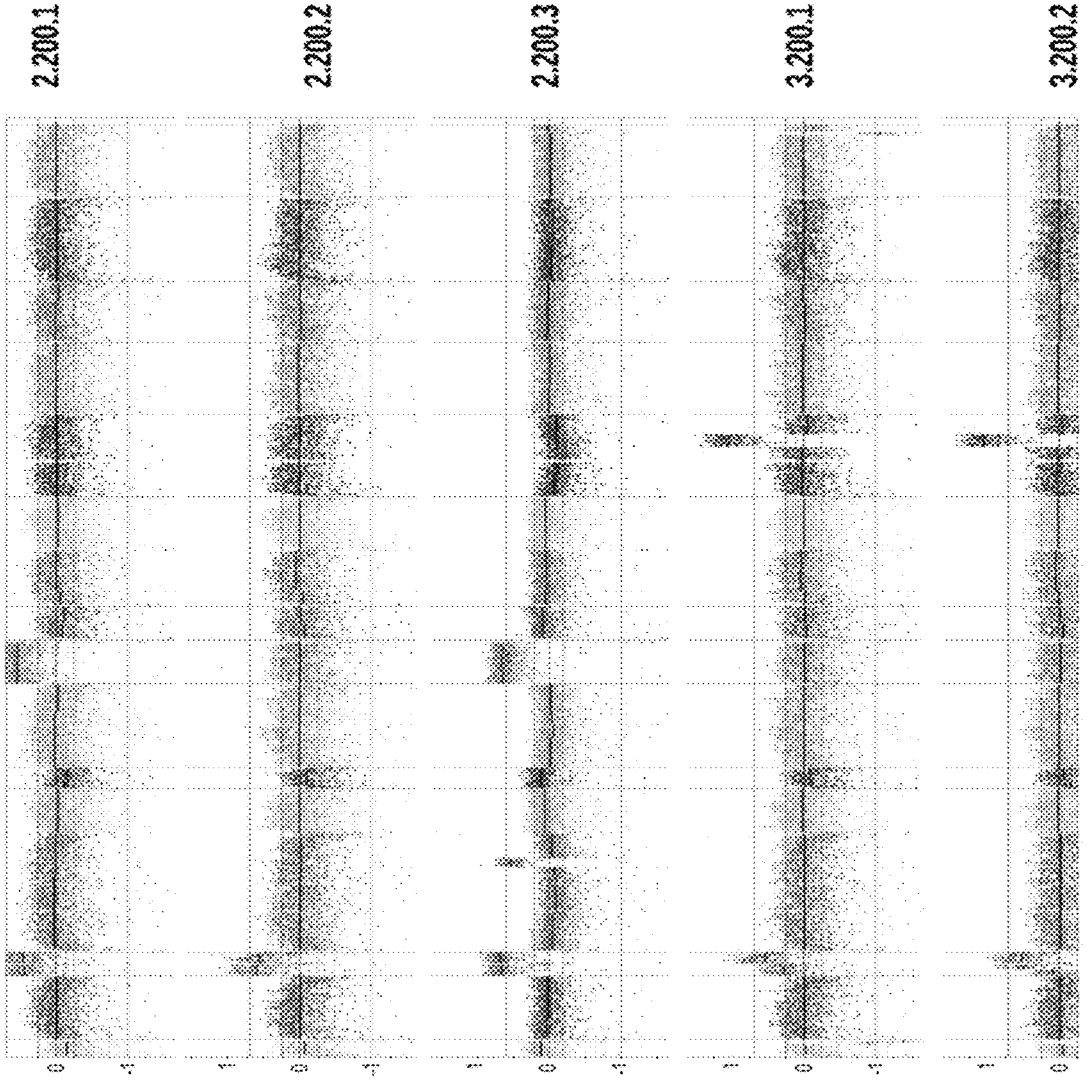
FIG. 5: Copy number variation in evolved clones of reactors 2 and 3 isolated at 200 generations. Genome view of yeast chromosomes and CNV patterns from a sliding window analysis. The y axis represents log 2 ratios of the coverage observed across 500 bp genomic windows to the coverage expected in a diploid genome without CNVs. Area of the plot located between the red lines (from −0.23 to −1) marks putative CNV loss events, whereas the region between the blue lines 270 (from 0.23 to 0.58) marks putative CNV gain events. It should be noted that the amplified region of chromosome XII observed in some of the clones does not correspond to the ribosomal DNA genes.

Whole Genome Sequencing of Adapted Clones Reveals Mutators and Extensive Aneuploidies After 2 years, yielding around 200 generations, evolved clones (excluding clones from reactors 2 and 6, which acquired a mutator phenotype, see below) contained, on average, 23 SNPs compared to the ancestral strain (data not shown). This number is higher than what would be expected based on measured rates of spontaneous mutations,[50] and could reflect an increased mutation rate under the stressful conditions imposed by the high ethanol levels in the set-up. Across all reactors and clones sequenced, a total of 8932 different mutated sites were identified. The largest fraction are SNPs (6424 out of 8932; 72%); Indels are found mostly in non-coding regions (1830 out of 2508; 73%), whereas SNPs are mostly found inside genes (4971 out of 6424; 77%). Most of these coding SNPs are non-synonymous (3672 out of 4971; 74%). In two reactors (reactor 2 and reactor 6), a marked increase in the number of mutations found in individual clones was noticed (see FIG. 4 and data not shown). Specifically, clones from reactor 2 contain a significantly higher number of indels (about 929 on average per genome for clones isolated after 200 generations, compared to 21 on average per genome for clones isolated after 200 generations in other reactors), whereas clones from reactor 6 display an increase in the number of SNPs (about 1765 per genome for clones isolated after 200 generations, compared to an average of 31 per clone for other reactors). This high number of mutations points to a so-called "mutator" phenotype typically present in cells with lower DNA replication fidelity and/or DNA repair. Interestingly, such mutators are frequently observed during evolution experiments, probably because mutators are more likely to acquire (combinations of) adaptive mutations faster.[23, 51-54] Interestingly, the increased mutation rate in reactor 2 is first observed around generation 70-80, coinciding with the appearance of a 21 bp insertion in the MSH2 gene, a key player in DNA mismatch repair. Mutations in MSH2 have been previously reported to confer a mutator phenotype,[55, 56] and mutations in MutS, the ortholog of MSH2 in *E. coli*, were identified in a long-term evolution experiment and also result in a mutator phenotype.[23] Indeed, deletion of this gene, as well as re-creating this insertion in an otherwise wild-type background, drastically increases mutation rate (data not shown). The MSH2 mutation eventually reaches a frequency of 100% at the end of the evolution experiment (200 generations). Apart from the convergence toward diploidy (see above), extensive copy number variation (CNVs) was also detected in the evolved clones, comprising both duplicated and deleted chromosomal regions (see FIG. 5 and data not shown). Other studies have observed similar copy number variation during adaptation to stress, including heat stress and specific nutrient limitations.[24, 28, 33] Interestingly, acquisition of an extra copy of chromosome III appeared to be a common feature for most of the evolved clones (data not shown). Some (parts of) other chromosomes, including chromosome XII and chromosome IV, are also duplicated in several of the evolved clones. These frequent occurrences indicate that these specific aneuploidies could be adaptive under ethanol conditions, although the exact mechanistic basis remains to be elucidated.

Figure 6:
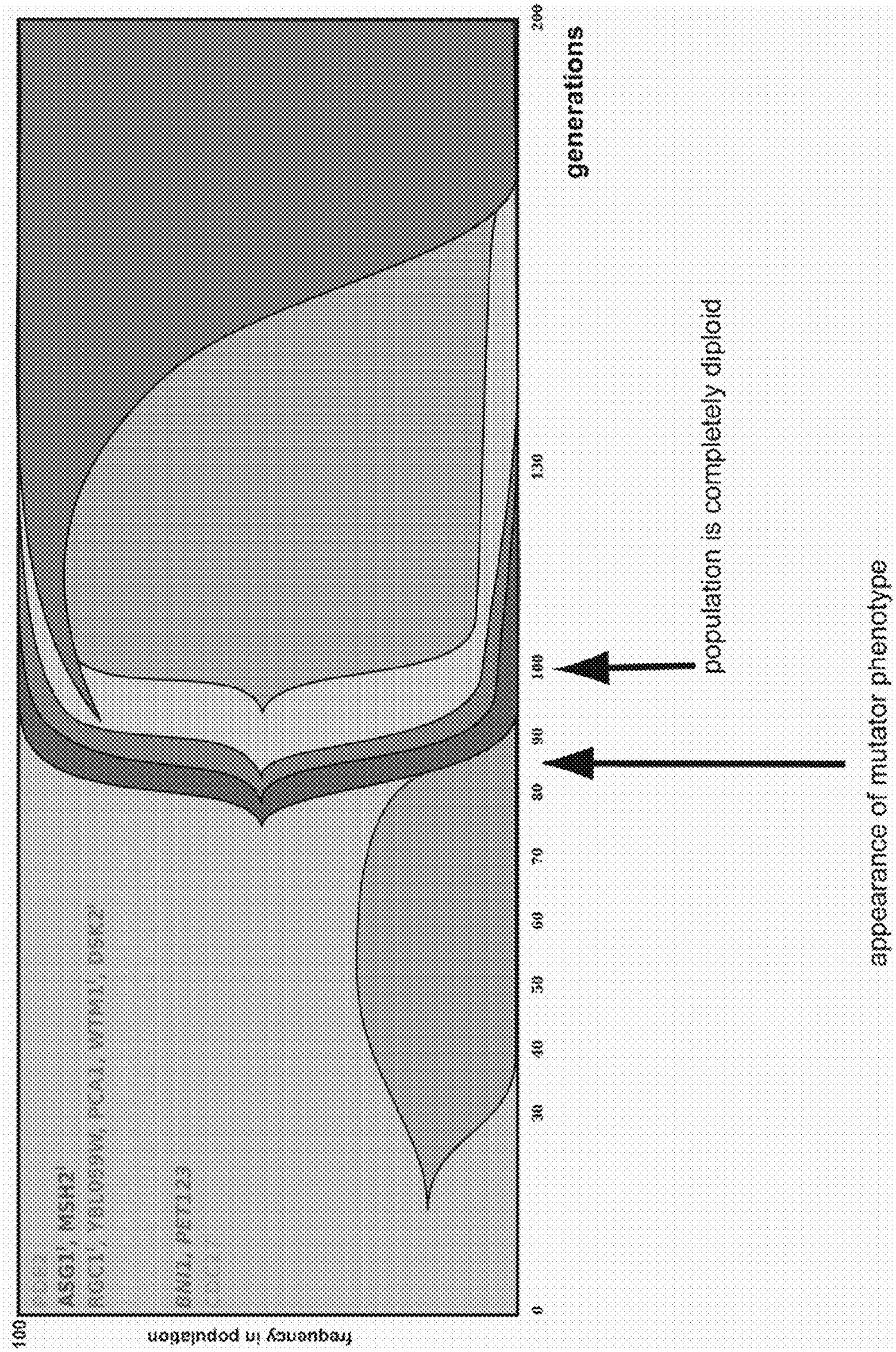
FIG. 6: Dynamics and linkage of mutations in evolved populations of reactor 2. Mutations (reaching a frequency of least 20% in the evolved population samples) and corresponding frequencies were identified from population sequencing data. Muller diagram represents the hierarchical clustering of these mutations, with each color block representing a specific group of linked mutations. Indels are designated with I, whereas heterozygous mutations are in italics. Mutations present as heterozygous mutations in all clones of a specific time point and present at a frequency of 50% in the population, are depicted as a frequency of 100% in the population, since it is expected that all cells in the population contain this mutation. After 80 generations, a mutator phenotype appeared in this reactor (indicated by arrow under graph), which coincides with the rise in frequency of an indel in the mismatch repair gene MSH2. Frequencies of haplotypes, dynamics and linkage for reactor 1 were calculated but are not shown.

Whole-Genome Sequencing of Evolved Populations Reveals Extensive Clonal Interference While the sequencing of clones yielded valuable information on individual lineages within the evolving populations, sequencing of evolving populations yielded more information on the complex mutational paths and dynamics between sub-populations within each evolving population. A distinct pattern of mutations appearing and disappearing over time in each of the six reactors was observed. Some of these mutations remain in the population, eventually reaching high levels or even complete fixation (i.e., presence in 100% of all cells in the population). Other mutations only persist for a short time until lineages carrying these mutations are outcompeted by others, so called "clonal interference." In total, 1637 mutations were identified across all populations and time points. 117 of these mutations are no longer present in the final time points sequenced, and 101 mutations drop more than 10% in frequency after reaching their maximum frequency, indicative of clonal interference. Interestingly, some overlap between the mutations found in different independently evolving populations was identified (i.e., in different reactors). Specifically, it was found that 20 genes mutated twice in different generations and populations, 3 genes mutated 3 times, 2 genes mutated twice, 2 genes mutated 5 times, and 1 gene mutated 6 times (data not shown). This significantly differs from what would be expected by chance (see Materials and Methods). Repeatedly hit genes are, amongst others, involved in stress response, cell cycle and heme biosynthesis. The higher number of sequenced samples from reactors 1 and 2 allowed further analysis of these population sequences and group mutations based on correlations in the changes in their respective frequencies (based on the pipeline described in reference [32]; see also, Materials and Methods). This yields a more detailed picture of the different co-evolving sub-populations present in these reactors, which is depicted in the Muller diagrams of FIG. 6 (and data not shown).

In both reactors, selective sweeps mostly consists of groups of mutations that move through the population together. While these reactors were inoculated with the same strain, the type and dynamics of mutations observed during adaptation appear very different. However, both evolving populations of reactor 1 and reactor 2 are characterized by strong clonal interference. In reactor 1, four different sub-populations are present around generation 90, each carrying different mutations. By generation 130, these lineages have been outcompeted by another lineage that almost completely dominates the population by 200 generations (data not shown). In reactor 2, a lineage carrying a mutation in PDE2 (encoding a high-affinity cAMP phosphodiesterase) is driven to extinction by a subpopulation carrying indels in ASG1 and MSH2. ASG1 is a transcriptional regulator involved in the stress response and has been found mutated in evolved populations from different reactors (including reactor 1; see also, FIG. 6, and data not shown). Another example of clonal interference is observed in the later generations of this reactor: a subpopulation carrying a mutation in CDC27 (encoding a subunit of the anaphase promoting complex/cyclosome) is driven to extinction by a subpopulation carrying mutations in BNI1 (important for nucleation of actin filaments) and PET123 (encoding a mitochondrial ribosomal protein).

Diverse Pathways Involved in Adaptation to Ethanol

The results discussed above revealed extensive variability in the type and number of mutations present in each evolving population. While this could suggest the presence of several, different mutational pathways (and thus lack of parallel evolution), mutations in different genes might affect identical or similar pathways, implying that the physiological adaptation to high ethanol might in fact be more similar than what is immediately apparent from the individual mutations. To gain insight into the affected biological pathways and investigate the possible similarities in adaptation to increased ethanol, different computational approaches were used. First, a term-enrichment analysis was performed on the complete list of mutated genes for all reactors (for enriched clusters, see Table 1 and data not shown). These enrichment methods have been used as one of the standard functional analysis tools and gave a first insight into potential adaptive pathways present in the evolved lineages.

TABLE 1

Top 10 functional clusters identified amongst genes hit by mutations in the evolution experiment. An enrichment score cutoff value of 1.3, equivalent to a p-value of 0.05 for term enrichment was used.[57]

| Cluster ranking | Cluster name | Enrichment score |
|---|---|---|
| 1 | ATP-binding | 3.54 |
| 2 | Cellular bud | 2.46 |
| 3 | Leucine-rich repeat | 2.23 |
| 4 | Mating projection | 1.79 |
| 5 | DNA damage response | 1.76 |
| 6 | Phosphorylation | 1.63 |
| 7 | ABC transporters | 1.60 |
| 8 | Regulation of cell shape | 1.47 |
| 9 | tRNA aminoacylation | 1.44 |
| 10 | Transcriptional regulation | 1.36 |

In a second step, a sub-network-based selection method was used[58, 59] (see Materials and Methods), first developed for *E. coli* expression data. Here, this method was adapted and extended to select the subnetwork from the global yeast interaction network that best connected the mutated genes in the most parsimonious way. This method also identifies the intermediary genes involved in signaling mechanisms, which are not necessarily mutated in the evolved lineages but mediate the cellular response. Mutations obtained from the populations with a mutator phenotype were excluded (reactors 2 and 6) because of their low signal-to-noise ratio. This analysis identifies genes frequently mutated in the different populations (DSK2, ASG1), as well as genes that are closely connected on the interaction graph (HEM3, HEM12, . . . ). This latter set reflects parallelism at the pathway level in the different reactors. From FIG. 7, it is also clear that sometimes multiple mutations occurring in the same pathway originated in the same reactor rather than across different reactors. This could indicate not only a level of parallelism between the different reactors but also between the sub-populations in the same reactor. To confirm this, the sub-network selection method was also separately applied on the mutations obtained for each of the populations. This confirms that within single populations, the same pathways seem to be affected as those that are consistently affected between the populations (including cell cycle, DNA repair and protoporphyrinogen metabolism, see also below). All resulting sub-networks as well as the enriched genes (including p-values) can be found in FIG. 7 (and data not shown). Additional analyses performed to increase mechanistic insight, including interactome analyses of genes containing non-synonymous mutations in the different population samples, as well as the effect of these mutations on protein functional domains, were also performed (data not shown).

Cell Cycle and DNA Replication

Figure 7:
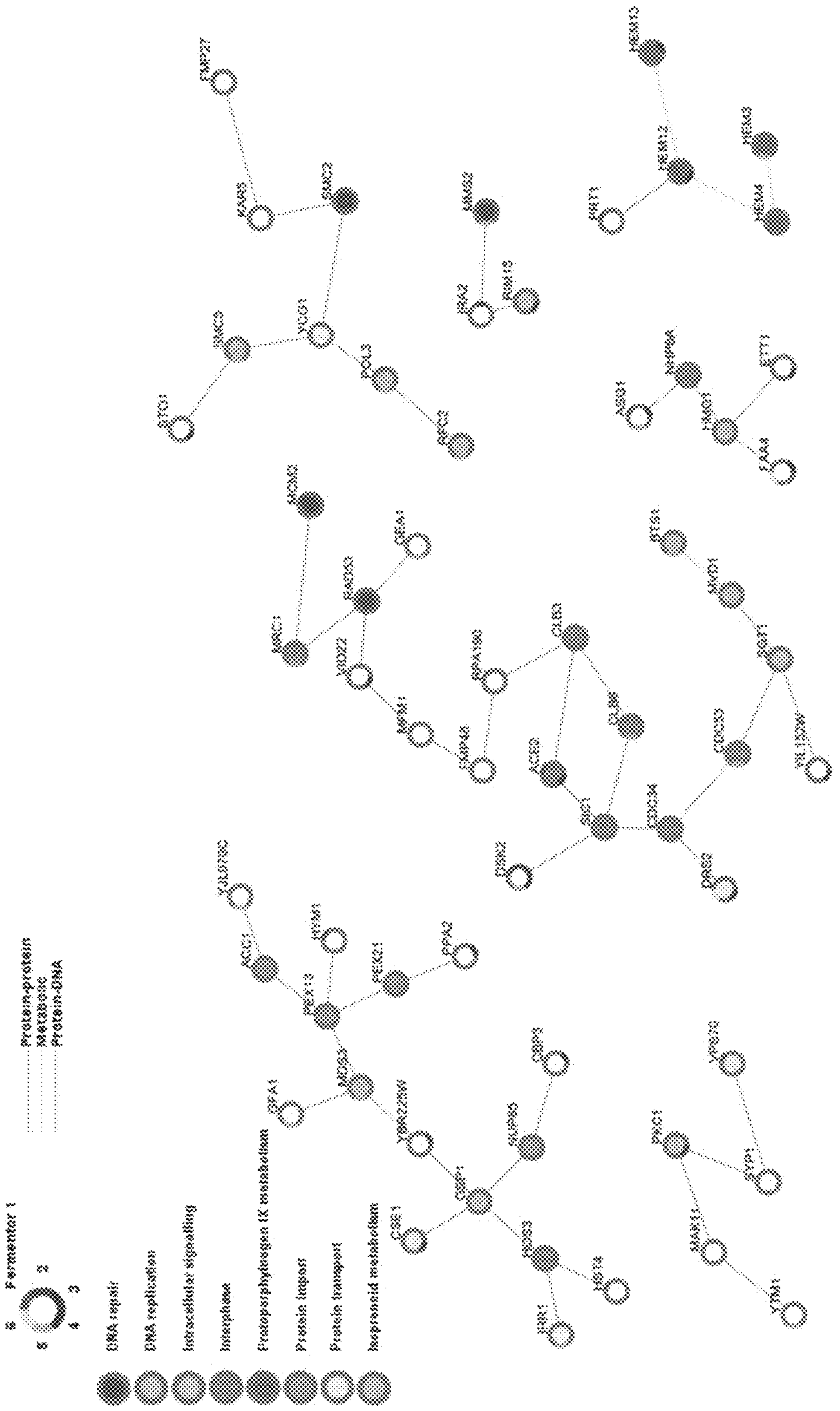
FIG. 7: Adaptive pathways are involved in cell cycle, DNA repair and protoporphyrinogen metabolism. Shown is the sub-network that prioritizes putative adaptive mutations by applying PheNetic on all selected mutations, excluding those originating from the populations with a mutator phenotype, i.e., reactors 2 and 6. The nodes in the network correspond to genes and/or their associated gene products. Node borders are colored according to the reactors containing the populations in which these genes were mutated. Nodes are colored according to gene function, for each gene the most enriched term is visualized (grey indicates no enrichment). Cell cycle-related processes have been subdivided into DNA replication and interphase. The edge colors indicate different interaction types. Orange lines represent metabolic interactions, green lines represent protein-protein interactions, and red lines represent protein-DNA interactions. Sub-networks were extracted by separately analyzing the mutated genes observed in each of the different populations (reactors)—this data is not shown here.

The analyses suggest that the cell cycle and DNA replication are affected in the evolved lineages (FIG. 7). Ethanol has been previously reported to delay cell cycle progression, probably through depolarization of the actin cytoskeleton.[60] This could be relevant for adaptation in the sense that slower growth could protect cells from stress, perhaps by inducing genes involved in the general stress response.[61-63]

Respiration

PheNetic analysis shows that protoporphyrinogen metabolism is affected in the evolved populations (FIG. 7). Since this is important for heme biosynthesis, this could indicate that respiration is affected downstream of mutations. Non-synonymous SNPs in functional domains or modified sites are expected to have more effect on the cell than mutations outside of these regions. It was found that such mutations in proteins involved in regulation and in enzymes of heme biosynthesis and proteins that need heme groups for proper functioning, are themselves involved in respiration (data not shown). These analyses point to a role for changes in respiration in adaptation to ethanol. Together, the results show evidence for parallel evolution, with the same processes (cell cycle and DNA replication) affected by different mutations, and also highlight the plethora of processes involved in increased ethanol tolerance in the adapted lineages.

Figure 8:
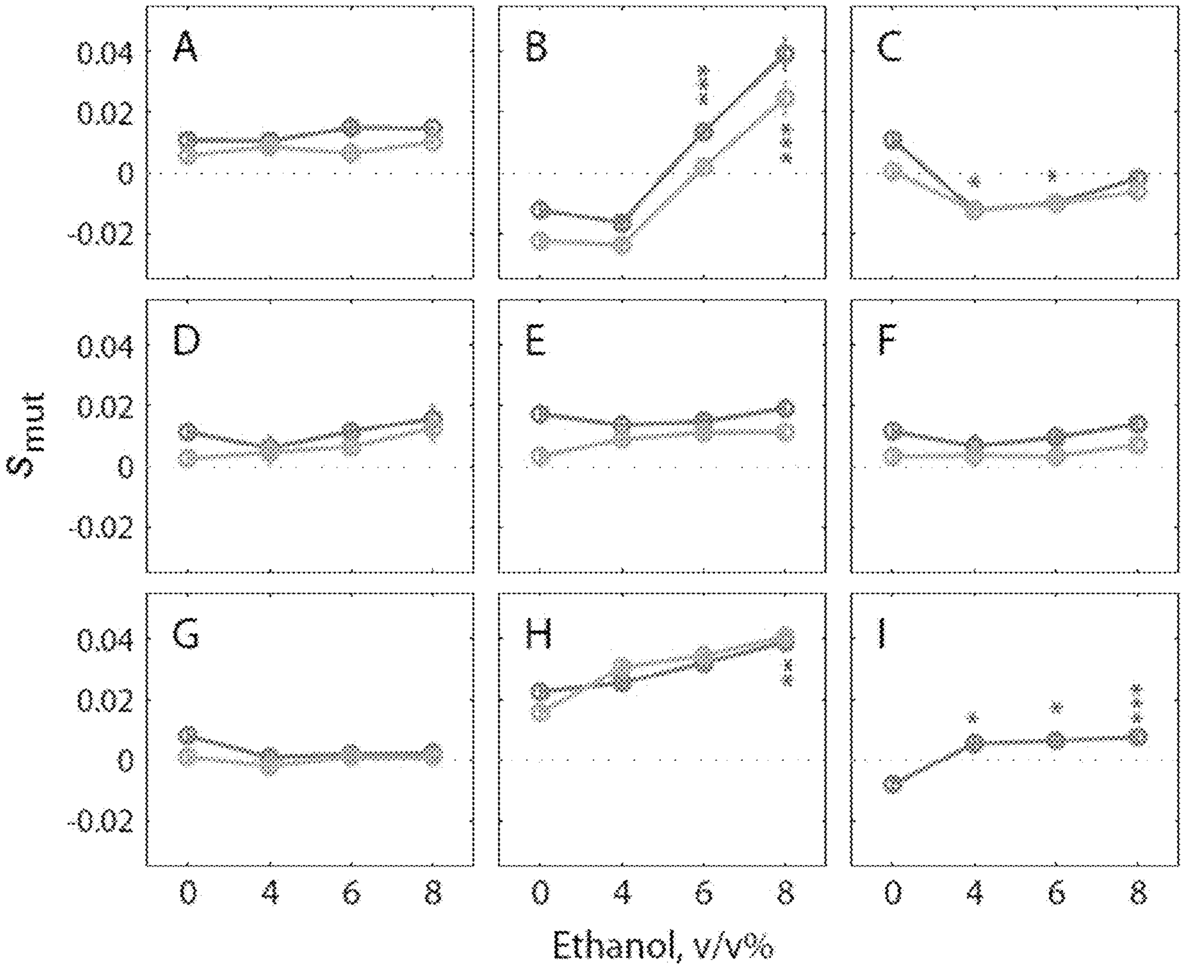
FIG. 8: Single mutations present in evolved populations can increase ethanol tolerance of a non-adapted strain. Plots show the average selection coefficient (smut) as a function of ethanol concentration for (Panel A) pca1$^{C1583T}$, (Panel B) prt1$^{A1384G}$, (Panel C) ybl059w$^{G479T}$, (Panel D) intergenic ChrIV A1489310T, (Panel E) hem13$^{G700C}$, (Panel F) intergenic ChrXII C747403T, (Panel G) hst4$^{G262C}$, (Panel H) vps70$^{C595A}$, and (Panel I) mex67$^{G456A}$. Superscripts denote the exact nucleotide change in each of the mutants tested. YECitrine-tagged mutants were competed with the mCherry-tagged parental strain (orange dots); dye-swap experiments were carried out by competing the mCherry-tagged mutants with the YECitrine parental strain (blue dots), except for (Panel I). Error bars show the S.E.M. from three experimental replicates. Asterisk shows P-values from the one-way ANOVA tests of the mean differences in 4-8% ethanol compared to fitness in 0% ethanol: * $p<0.05$;  $p<0.01$; *$p<0.005$.

Example 2. Several High-Frequency Mutations Increase Ethanol Tolerance of Non-Evolved Strain The high number of mutations (both SNPs and Indels) precluded an exhaustive analysis of all mutations present in the tolerant clones and populations and their effect on ethanol tolerance. One commonly used approach to investigate putative beneficial mutations is backcrossing of evolved clones to their ancestor, which does not contain any mutation. However, since each of the evolved populations proved unable to form any spores, this strategy was not accessible. Hence, the focus was on SNPs reaching high frequencies in the 200-generation population samples. In total, nine SNPs were selected for further study (Table 2). Several of the mutated genes belong to or are linked to the processes affected across and/or within specific reactors (heme metabolism, protein transport and cell cycle, see also Table 2). These nine SNPs were subsequently introduced into the ancestral haploid strain. The effect of these mutations was assessed by high-throughput competition experiments,[64] in 0, 4, 6 and 8% (v/v) EtOH conditions, with glucose as a carbon source (FIG. 8, data not shown). Several mutants show a clear increase in fitness, with the fitness effect often depending on the concentration of ethanol in the medium. Most mutants show slightly increased fitness in medium without added ethanol, with further increases in relative fitness with increasing exogenous ethanol concentrations. Mutants in PRT1 and MEX67 are less fit than the WT in non-ethanol conditions, but show increased fitness in higher ethanol levels. MEX67 is a poly (A) RNA binding protein involved in nuclear mRNA export. PRT1 encodes the eIF3b subunit of the eukaryotic translation initiation factor 3 (eIF3). The increased ethanol tolerance associated with these mutations hints at translation processes as targets of ethanol. Interestingly, a recent study in *E. coli* showed that ethanol negatively impacts transcription as well as translation.[6] However, if and how mutations in MEX67 and PRT1 might mitigate this effect and contribute to ethanol tolerance remains unknown.

TABLE 2

SNPs in evolved lineages selected for introduction in non-ethanol- tolerant strain. SNPs reaching high frequencies in the different evolved lineages were introduced in a haploid, non-ethanol tolerant strain. Gene functions were obtained from SGD, worldwideweb at yeastgenome.org.

| Location | SNP type | Nucleotide change | Function of mutated gene (SGD) | Enriched process involved in |
|---|---|---|---|---|
| Reactor 1 | | | | |
| ChrIV: 1489310 | Intergenic | A > T | | NA |
| HST4 | Non-synonymous | G262C | Histone deacetylase, involved in cell cycle progression, SCFA metabolism | Cell cycle* |
| VPS70 | Non-synonymous | C595A | Vacuolar protein sorting, unknown function | Protein transport* |
| Reactor 2 | | | | |
| YBL059W | Non-synonymous | G479T | Unknown function | NA |
| PCA1 | Non-synonymous | C1583T | P-type cation-transporting ATPase | Heme biosynthesis?* (potential role in iron homeostasis) |
| Reactor 3 | | | | |
| ChrXII: 747403 | Intergenic | C > T | | NA |
| HEM13 | Non-synonymous | G700C | Heme biosynthesis | Protoporphyrinogen metabolism/heme biosynthesis* |
| Reactor 5 | | | | |
| PRT1 | Non-synonymous | A1384G | eIF3 subunit, essential for protein synthesis | NA |

TABLE 2-continued

SNPs in evolved lineages selected for introduction in non-ethanol- tolerant strain. SNPs reaching high frequencies in the different evolved lineages were introduced in a haploid, non-ethanol tolerant strain. Gene functions were obtained from SGD, worldwideweb at yeastgenome.org.

| Location | SNP type | Nucleotide change | Function of mutated gene (SGD) | Enriched process involved in |
|---|---|---|---|---|
| Reactor 6 | | | | |
| MEX67 | Non-synonymous | G456A | Component of nuclear pore, mRNA export | NA |

*Enriched process identified by PheNetic analyses across all reactors

Of all mutations introduced into the ancestral strain, vps70C595A provided the largest fitness increase. VPS70 is putatively involved in sorting of vacuolar carboxypeptidase Y to the vacuole.[65] A mutation in VPS70 has been recently identified by members of the team as a determinant of ethanol tolerance in a Brazilian bioethanol strain.[66] Interestingly, the VPS70 mutation in the evolved ethanol-tolerant lineages alters the same amino acid as the mutation present in the industrial ethanol-tolerant strain (A. Goovaerts and J. M. Thevelein, personal communication). The fact that one of the mutations identified in the evolved lineages was also found in an industrially used bio-ethanol strain underscores the potential of the approach to find biologically relevant mutations for increased ethanol tolerance. Other members of the VPS family have been previously implicated in ethanol tolerance as well, but also here, the exact molecular mechanism through which they could increase ethanol tolerance is still unclear.[10, 12, 67] As far as is known, none of the other genes investigated in this study have been previously implicated in ethanol tolerance nor have these mutations been found in natural or industrial yeasts so far. This implies that these mutations could be prime candidates to improve the ethanol tolerance and production of existing industrial yeasts.[68]

Example 3. Testing of Mutations in Industrial Reference Strain

As a next step, the seven coding mutations shown in Table 2 (identified with a lab yeast strain) were introduced into the industrial reference biofuel strain Ethanol Red, a diploid *Saccharomyces cerevisiae* strain. For each of the coding mutations, the two wild-type alleles in Ethanol Red were replaced with two mutant alleles (more details can be found in the materials and methods section). Next, maximal ethanol accumulation in YP+35% (w/V) glucose was determined for each of these mutant strains.

Figure 9:
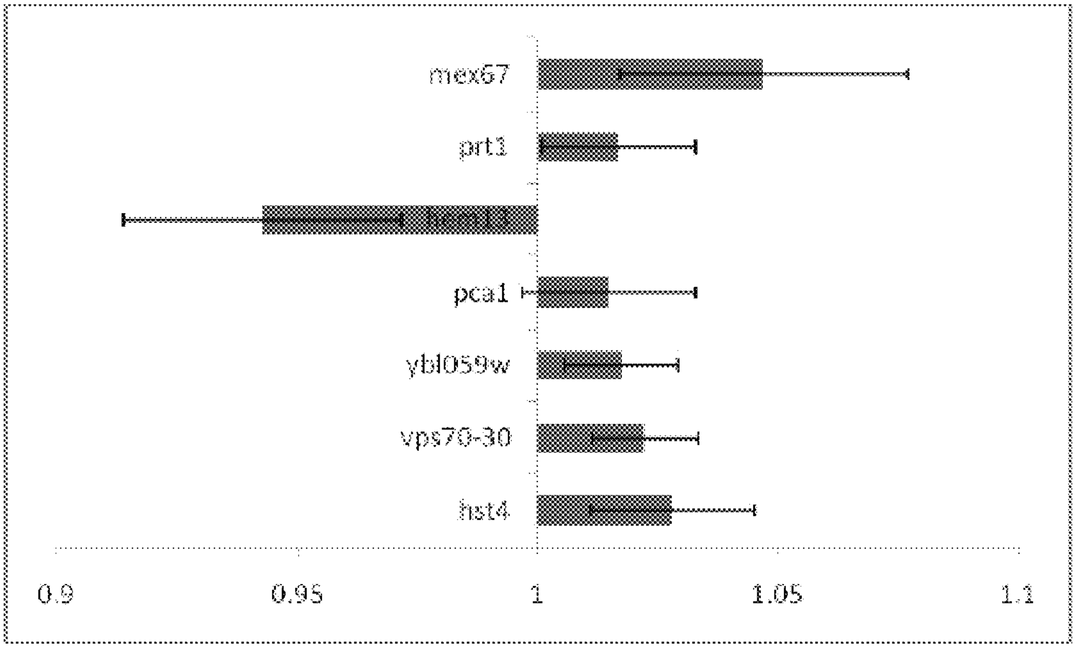
FIG. 9: Mutations identified in lab strains also increase alcohol tolerance in an industrial reference strain. Coding mutations were introduced into the industrial reference biofuel strain Ethanol Red. Ethanol production of these mutants is shown, relative to its proper control. All experiments were repeated four times (real biological replicates, using independent transformants where available).

The relative ethanol production of these mutants is summarized in FIG. 9.

All but one of the mutants yielded higher ethanol titers. Statistical significance was reached for the mex67 mutant. This mutation showed the highest relative increase in the industrial strain. Of note, the relative increase in ethanol yield of around 4% is not 4% ABV extra, but an increase of 4% compared to the proper control. In practice, this corresponds to approximately 0.8% alcohol extra. All experiments were repeated four times (real biological replicates, using independent transformants where available).

Figure 10:
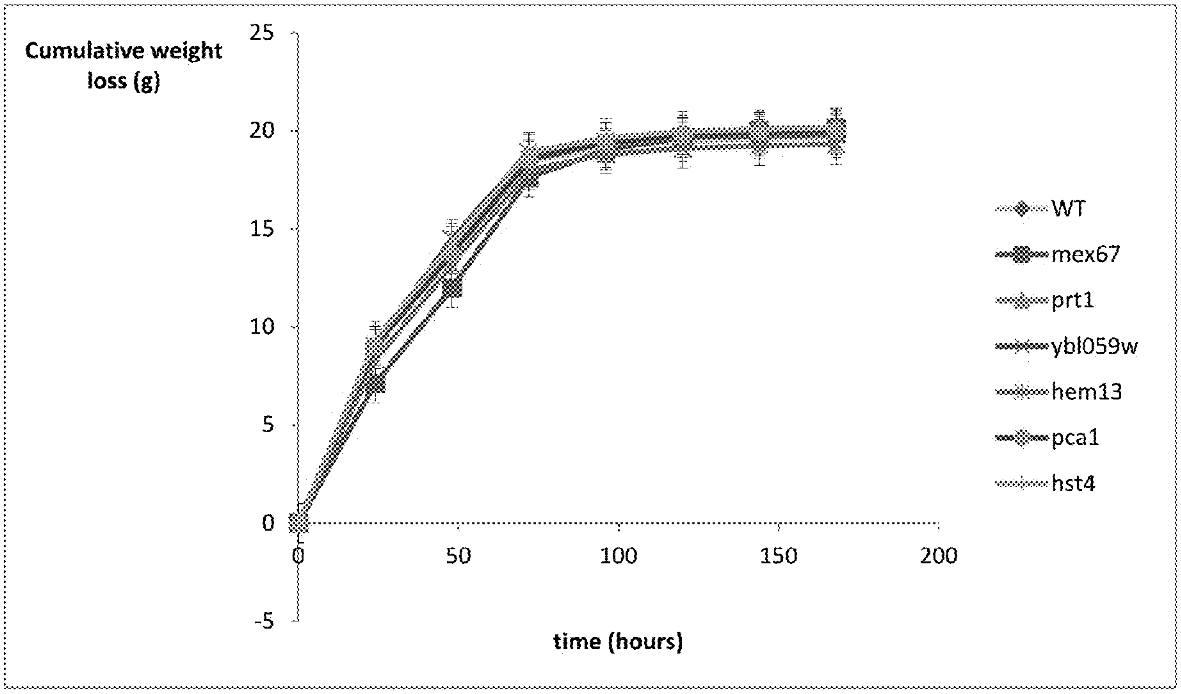
FIG. 10: Fermentation performance of mutant strains is comparable to wild-type strain. Coding mutations were introduced into the industrial reference biofuel strain Ethanol Red. Fermentation performance in YP+35% glucose (w/v) is shown as the cumulative weight loss—a proxy for $CO_2$ production—during the fermentation. Each line represents the average of four replicate fermentations, error bars represent standard deviation.

Fermentation capacity in YP+35% glucose (w/v) of each of the mutants was comparable to that of the wild-type Ethanol Red strain. Fermentation capacity of these mutants is summarized in FIG. 10.

DISCUSSION

Many fundamental questions on the dynamics and genetics of adaptation to a complex and severe stress such as ethanol are still unanswered. Which type and number of mutations are needed and/or sufficient? To what extent are these mutations and the pathways they affect predictable? To address these questions, high-coverage whole-genome sequencing of clones and populations was performed, isolated throughout a two-year evolution experiment and characterized their adaptation to increasing ethanol levels. This allowed painting a detailed picture of the mutational dynamics in the evolving lineages.

The study demonstrates how many different evolutionary mechanisms all come together to provide adaptation to a severe and complex stress. Specifically, it was found that adaptation to high ethanol levels involves changes in ploidy, copy number variation and the appearance of mutator phenotypes, with evolving populations showing strong clonal interference. Although these mechanisms have been observed in other studies (see, for example, references 24, 27, 32, and 69-71), different mechanisms are often observed and/or studied separately. More importantly, in traditional evolution studies, populations are exposed to a fixed concentration of antibiotic or limiting nutrient. Under these conditions, selection pressure is reduced or even eliminated when cells become resistant. In the experimental set-up, ethanol levels were stepwise increased over time so that cells were evolving under constant selection. High concentrations of ethanol also actively kill non-tolerant cells, so that cells not adapted to the higher ethanol concentrations die and/or are washed out of the turbidostat. Taken together, the study combines aspects of traditional evolution studies with principles used in morbidostat experiments.[27] Under such severe stress conditions (near-morbidostats), the number of generations may not be the ultimate way of measuring evolutionary time; cell death and mutations that are not associated with DNA replication become increasingly important, which could result in quick sweeps.

Extensive variation in genome size in the evolved cells was found, with aneuploidies in a large number of the evolved clones as well as convergence toward a diploid state in the initial haploid and tetraploid populations. Becoming diploid thus appears to be a frequently used strategy by cells of different ploidy, which effectively increases ethanol tolerance. Convergence to diploidy has been observed in other laboratory evolution experiments.[25, 36, 72] In contrast to these studies, a clear fitness advantage of the diploid strains in ethanol was demonstrated. Although further research is needed to fully understand this fitness advantage, changes in gene expression and/or cell size could be important factors contributing to the increased fitness of diploid cells.[41, 73, 74]

Unfortunately, this convergent evolution prevented a detailed analysis from being performed on the difference in adaptive strategies employed by haploids, diploids and tetraploids to increase ethanol tolerance.

Aneuploidy and copy-number variation are increasingly recognized as common themes in rapid adaptation.[24, 28, 69, 70] It is believed that changes in the copy number of chromosomes or chromosomal fragments provide a relatively easily accessible way to change expression levels of specific key genes,[75, 76] and these CNVs can provide large, usually condition-specific, fitness effects.[77] However, such large-scale changes in the genome likely also have some unwanted, detrimental side effects, such as imbalance between gene products and genome destabilization.[78-80] Evolving populations are believed to gradually replace adaptive CNVs with more specific mutations that show fewer pleiotropic effects.[28] Notably, several of the evolved clones, isolated from different reactors, carry an extra copy of chromosome III and/or chromosome XII, pointing toward a potential adaptive benefit of this specific aneuploidy. Interestingly, it was found that clones isolated at later time points have a specific, smaller region of chromosome XII amplified (data not shown), indicating a more refined solution. GO enrichment and network analyses of the repeatedly amplified region of chromosome XII (position 657500-818000) hints at cell wall formation as one of the key processes affected by these amplifications. Previous studies have indeed shown that cell wall stability is a key factor involved in ethanol tolerance.[18]

Apart from diploidization of the evolving lineages, another example of parallelism at the phenotypic level is the appearance of a mutator phenotype in two of the six evolving populations. The sweep of the MSH2 mutation in reactor 2 is likely caused by a so-called hitchhiking event, with the high mutation rates in the MSH2 mutant leading to the appearance of one or several beneficial mutations that drive the selective sweep. Because of the lower temporal resolution of sequenced population samples of reactor 6, identifying the allele(s) underlying the mutator phenotype in this reactor has proven to be difficult. Parallelism at the genotypic level is less clear: few mutations and mutated genes shared between the different evolved lineages was found. Applying different types of network and enrichment analyses revealed functional modules affected in several of the adapted populations. These pathways include response to stress, intracellular signal transduction, cell cycle and pathways related to membrane composition and organization (such as isoprenoid metabolism, glycerophospholipid catabolism and fatty-acyl-coA metabolism). For some of these pathways, further work is needed to clarify their exact involvement in ethanol tolerance.

To investigate the phenotypic effect of mutations present in the evolved lineages, high-throughput fitness measurements in different ethanol concentrations was performed. While the evolved lineages contained multiple mutations, single mutations reaching high frequency in the evolved populations could already significantly increase ethanol tolerance when introduced into the ancestral, non-evolved haploid strain. Moreover, several of these single mutations selected for further study also showed a (modest) fitness benefit in conditions with no ethanol, with greater increases as ethanol levels rise. The number of mutations identified in this study was too large to investigate the fitness effect of each individual mutation.

However, the strategy to select mutations that reached fixation in the evolved populations clearly proved successful, identifying as many as seven mutations (out of nine tested) that confer a fitness advantage in high ethanol environments. Mutations in genes linked to processes identified as affected across the different reactors—protein transport (VPS70) and heme metabolism (HEM13 and PCA1)—indeed increased fitness in EtOH. This underscores the potential of PheNetic, a sub-network-based selection method for identifying adaptive mutations. Two of the mutations tested, ybl059wG479T and hst4G262C, did not increase fitness, although they reached high frequency in the adapted populations. This is indicative of hitch-hiking with other, beneficial mutations, or possible epistatic interactions with other mutations.

Why then would not all feral yeasts show high ethanol tolerance, if it appears so easy to attain? First, it seems plausible that not all yeasts are confronted with selection for high ethanol tolerance. Furthermore, it is important to note that the fitness of the mutants under many different conditions that mimic the natural habitats of yeasts has not been tested. It seems likely that some of the mutations identified in this study would result in lower fitness in other environments.[81, 82] Moreover, the effect of combined mutations has not been investigated. While it is possible that combining different mutations could increase ethanol tolerance even further, it also seems likely that some mutations and/or specific combinations of mutations could lead to reduced fitness in different low and/or high ethanol environments. Indeed, while the clones have increased fitness in EtOH, fitness of several of the evolved clones (containing multiple other mutations apart from the ones investigated in this study) decreased in medium without exogenous EtOH (data not shown). These results are indicative of antagonistic pleiotropy: the specific mutations present in the evolved clones increase fitness in one condition (high ethanol, which was selected for), whereas they reduce fitness in other environments. Ethanol resistance is an important trait for the survival of feral yeasts in nature because the ethanol produced inhibits growth of competing microorganisms, while it serves as a carbon source in later stages of growth, when all fermentable sugars are depleted (the so-called "make-accumulate-consume strategy"[83-85]). The results suggest that adaptation to high ethanol is complex and can be reached through different mutational pathways. Apart from yielding insight into the evolutionary mechanisms leading to such complex and ecologically important phenotypes, the study is also of considerable industrial importance. Several of the mutations identified in this study may be useful to increase the ethanol tolerance of industrial strains used for the production of alcoholic beverages or biofuels.

Materials and Methods

Strains Used in this Study

Starting strains for the evolution experiment are all derived from the haploid prototrophic S288c strain FY5.[86] To prevent clumping of cells during the evolution experiment, the flocculation genes FLO1, FLO10 and FLO11 were deleted in this strain using deletion cassettes based on pUG6, conferring resistance to G-418 disulfate.[87] Markers were removed through the Cre/LoxP technique using pSH65.[88] Mating type switching of this strain was then performed, using plasmid pSB283, to create isogenic diploid and tetraploid strains. Fluorescent versions of strains (YECitrine or mCherry tagged) were constructed by integrating fluorescent markers at an intergenic, neutral region of chromosome II.

Long-Term Selection

Populations were founded in 400 mL ethanol-containing media. Media contained 10 g/L yeast extract, 20 g/L bacto-peptone, 4% (w/v) glucose, 0.001% (v/v) Rhodorsil, Anti-foam Silicone 46R, chloramphenicol (50 μg/mL) and increasing concentrations of ethanol. Populations were maintained at an average population size of $10^{10}$ cells. After 25 generations, the level of EtOH in the media was increased each time (starting at 6% (v/v) and reaching 12% at 200 generations).

Turbidostat cultures were maintained using Sixfors reactors (INFORS®) at 30° C., pH was kept constant at 5.0 with continuous mixing at 250 rpm in aerobic conditions. At regular times, a population sample was obtained from each of the cultures for further analyses and stored in glycerol at −80° C. For DNA extraction purposes, a population cell pellet was also frozen down at −80° C.

Fitness Determination

Fitness for all evolved strains was determined in rich medium (YP, 2% (w/v) glucose) with 9% (v/v) ethanol, by competing strains against a YECitrine labeled ancestral strain. Cultures were pre-grown in YPD 6% ethanol. After 12 hours, wells of a 96-deep well plate were inoculated with equal numbers of labeled reference and unlabeled strains (approximately $10^6$ cells of each) and allowed to grow for around 10 generations. Outer wells only contained medium and acted as a buffer to prevent ethanol evaporation. Additionally, plates were closed with an adhesive seal and plastic lid, and parafilm was used to prevent ethanol evaporation. Cultures were regularly transferred to new medium to prevent nutrient depletion. The ratio of the two competitors was quantified at the initial and final time points by flow cytometry. Data analysis was done in FLowJo® version 10. Measurements were corrected for the small percentage of labeled, non-fluorescent cells that occurred even when the reference strain was cultured separately as well as for the cost of YFP expression in the labeled reference strain. For each fitness measurement, three independent replicates were performed. The selective advantage, s, of each strain was calculated as s=(ln(Uf/Rf)−ln (Ui/Ri))/T where U and R are the numbers of unlabeled and reference strain, respectively, the subscripts refer to final and initial populations and T is the number of generations that reference cells have proliferated during the competition. The fitness of the unlabeled WT strain was designated 1, fitness of the evolved strains as 1+s.

Determination of Cell Ploidy

DNA content of evolved populations and evolved clones was determined by staining cells with propidium iodide (PI) and analyzing 50,000 cells by flow cytometry on a BD Influx. The ancestral haploid and diploid strains used in the evolution experiment were used for calibration.

Whole Genome Sequencing

For evolved populations, genomic DNA was directly extracted from pellets that were frozen at the time of sample taking. Evolved clones were selected from the different population samples by streaking glycerol stocks from the corresponding population samples on YPD plates. Swabs from each population were subsequently grown in YPD 6% EtOH and dilutions were plated on YPD plates with different ethanol concentrations (ranging from 8% to 10%; with a 0.5% stepwise increase in ethanol concentrations). From these plates, ethanol-tolerant clones were selected and genomic DNA of these clones was extracted. Genomic DNA was prepared using the QIAGEN® genomic tip kit. Final DNA concentrations were measured using QUBIT®. Paired-end sequencing libraries with a mean insert size of 500 bp were prepared and libraries were run on an ILLUMINA® HiSeq® 2000 (EMBL GeneCore facility, Heidelberg). Average sequencing coverage for clone and population sample is 80X and 500X, respectively.

Variant Calling, Filtration and Annotation

Adaptors removal and reads quality control were done by Trim Galore! (worldwideweb at bioinformatics.babraham.ac.uk/projects/trim_galore/) with options (-q 30-length 50). The clean reads were then mapped reference *S. cerevisiae* genome (S288C, version genebank64) using Burrows Wheeler Alignment allowing maximum 50 bp gaps.[89] To identify mutations, the BROAD Institute Genome Analysis Toolkit 628 (GATK, version 3.1) was used.[90] Performance of local realignment of reads around Indels was begun, in order to eliminate false positives due to misalignment of reads, which was followed by a base recalibration step. Then, SNP and Indel calling according to the GATK best practice recommendations was performed. Population samples and single clone datasets were analyzed independently. For population data, Indel calling was performed using the UnifiedGenotyper tool, and the identified variants were filtered based on the recommended criteria (QD<2.0, FS>200.0, ReadPosRankSum<−20 and InbreedingCoef<−0.8). For the SNPs, the UnifiedGenotyper was used to perform multi-sample SNP calling on all the population samples together. The resulting multi-sample callset was then used as a prior call to SNPs in all individual samples. The called SNPs were then subject to filtering (QD<2.0, FS>60, ReadPosRankSum<−8.0, MQ<40, MQRankSum<−12.5). Furthermore, the SNPs that were called inside regions containing Indels were filtered out. A list of all known repetitive regions and low complexity regions was generated using the program RepeatMasker (worldwideweb at repeatmasker.org/cgibin/WEBRepeatMasker), which were masked out from the assemblies. Finally, variants present in the ancestral strain were filtered out from all samples. A similar approach was used to analyze the clonal samples. Ploidy level of each isolated clone was determined by PI staining and variant calling was performed with UnifiedGenotyper for haploid clones or HaplotypeCaller for diploid clones. Subsequently, SNPs and Indels were filtered based on the GATK best practice recommendations as mentioned above. The inbreeding coefficient filter was excluded in the clonal sample filtering for Indels, as it is a population-level metric. Annotation and effect prediction of all identified variants was performed using snpEff.[91] Final processing of the data was performed using an R script, which involved filtering out variants called within the sub-telomeric regions (15 kbps from the chromosome ends) and, for population samples, variants whose frequency did not change by more than 10% during the experiment. The infrastructure of the VSC—Flemish Supercomputer Center was used for these analyses. For improved performance, CPU multithreading (-nct) capabilities of GATK were utilized, providing up to 20 cores and maximum memory capacity of 64 GB per process.

Identification of Copy Number Variations (CNV)

CNVs in the samples were identified using *Nexus* Copy Number software, version 7.5 (worldwideweb at biodiscovery.com/software/*nexus*-copy-number). Reads were accumulated in 500-base bins along all chromosomes, rejecting bins with less than ten reads. Log 2 ratios of copy numbers were then estimated from the read-depth counts in these intervals. The following calling parameters were used: minimum number of probes per segment of 5, significance threshold of p-value=1×10^−9, percentage of removed outliers of 5% and the limits for copy gain and loss of +0.25 and −0.25, respectively.

Statistical Analyses of Genes Hit Multiple Times

The p-values probabilities of genes being hit by a mutation a specific number of times were calculated using the binomial distribution. The number of draws was set to the total number of mutations found inside coding regions (i.e., 817); the number of successes was set to the number of times a specific gene was hit by a mutation (2 to 6); the probability of success was set to the specific ratio of the length of each gene hit multiple times (in nucleotides) over the entire coding content of the *S. cerevisiae* genome (9080922 nucleotides).

Haplotype Reconstruction

Haplotype reconstruction was based on the approach described in reference [32]. Prior to the actual reconstruction, variants identified in the sequencing data were subject to further processing by excluding variants that were multiallelic, variants that exhibited mixed zygosity in the isolated clones (i.e., homozygous in one clone and heterozygous in another clone) and variants that did not reach the frequency of 0.2 at any point during the experiment. Haplotypes (or "mutational cohorts") present in the remaining variants were next reconstructed using a MATLAB® script (kindly provided by the Desai lab) on a local machine running MATLAB® 2013a. Briefly, variants present in the dataset were clustered into haplotypes based on the Euclidean distance between their frequencies at specific time-points of the experiment. Afterward, frequencies of individual variants assigned to a specific haplotype were averaged to obtain the frequency of the haplotype itself. Frequencies of the identified haplotypes at specific time points (data not shown) were then used as source data to draw their approximate Muller diagram representations with INKSCAPE® 0.48.4.

Enrichment and Network Analysis

Functionally meaningful terms enriched in the list of genes hit in the evolution experiment were identified using DAVID Tools.[57, 92] Overall, 170 clusters of functionally meaningful terms were identified, of which ten passed the statistical enrichment criteria. An enrichment score cutoff value of 1.3 was used, equivalent to a p-value of 0.05 for term enrichment, as recommended in reference [57].

PheNetic Analyses

Intergenic mutations were discarded for the analysis. The interaction network used as input for PheNetic was composed of interactomics data obtained from KEGG[93] for metabolic interactions, String for protein-protein interactions[94] and Yeastract for protein-DNA interactions.[95] The total interaction network contains 6592 genes and 135266 interactions. This interaction network was converted to a probabilistic network using the distribution of the out-degrees of the terminal nodes of the network edges. By doing so, edges connecting nodes with a low out-degree will receive a high probability while edges connecting nodes with a high out-degree receive a low probability. Using lists of mutated genes as input, PheNetic will now infer that sub-network of the probabilistic network that best connects the mutated genes in the list over the probabilistic network. As the probabilistic network penalizes hub nodes, the inferred sub-network will, therefore, preferentially connect the mutated genes through the least connected parts of the network. This results in selecting the most specific parts of the network that can be associated with the mutated genes.

PheNetic was used to connect the mutated genes over the interaction network[58] with the following parameters: 100-best paths with a maximum path length of 4 were sampled between the different mutations in combination with a search tree cutoff of 0.01. As the size of the selected sub-network by PheNetic is dependent on both a cost parameter and the number of mutated genes in the input, different costs were used for the sub-network inference from different sizes of mutated gene lists. For the sub-network inference between all the mutated genes from the non-mutator reactors, a cost of 0.25 was used, for the non-mutator reactors (1, 3, 4, 5), a cost of 0.05 was used as they all have a similar amount of mutated genes, and for the mutator reactors (2 and 6), a cost of 0.5 was used.

Network Visualization and Enrichment

The resulting networks were visualized using CYTOSCAPE® and a functional enrichment using the biological process terms of Gene Ontology in combination with the annotation of SGD of the sub-networks was performed using the Bingo plugin, version 2.44.[96]

Construction of Mutant Strains

Selected mutations identified from the whole-genome sequencing data were introduced into the ancestral genetic background using the following protocol. First, a selectable marker conferring resistance to hygromycine was introduced near the genomic location of interest through homologous recombination. Part of this locus was then amplified together with the selectable marker using a forward primer containing the desired mutation. The resulting PCR product was then transformed into the ancestral strain; and presence of the mutation was verified by Sanger sequencing.

High-Throughput Competitive Fitness Measurements

YECitrine- or mCherry-tagged site-directed mutant strains were competed with the parental mCherry- or YECitrine-tagged strains, respectively, as described in reference [64]. In brief, saturated cultures of mutant and parental strains were mixed in equivalent volumes and inoculated onto 150 μl of YNB-low fluorescent medium in 96-well microtiter plates (CORNING® 3585). Micro-cultures grew without shaking and were serial-diluted every 24 hours for approximately 28 generations (7 days) in a fully automated robotic system (TECAN® Freedom EVO200) that integrates a plate carrousel (LICONIC® STX110), a plate reader (TECAN® Infinite M1000), a 96-channel pipetting head, an orbital plate shaker, and a robotic manipulator arm. The equipment was maintained in an environmental room at constant temperature (30° C.) and relative humidity (70%). Fluorescence signal (mCherry: Ex 587 nm/5 nm and Em 610 nm/5 nm; YECitrine: Ex 514 nm/5 nm and Em 529 nm/5 nm) and absorbance at 600 nm were monitored every hour during the entire experiment. The YECitrine- or mCherry-tagged parental strains were competed to each other for normalization and monitored individually to determine background fluorescence signal. Fluorescence and absorbance output data was analyzed in MATLAB® as described in reference [64] to obtain an average selection coefficient, smut, with its S.E.M. from three experimental replicates.

Introduction of Selected Alleles in Ethanol Red

Selected mutations identified from the whole-genome sequencing data were introduced into the diploid strain Ethanol Red using the following protocol. First, a selectable marker conferring resistance to hygromycin was introduced near the genomic location of interest through homologous recombination. Part of this locus was then amplified together with the selectable marker using a primer containing the desired mutation. The resulting PCR product was then transformed into Ethanol Red; and presence of the mutation was first identified by PCR using 3' mismatch primer pairs, and subsequently verified by Sanger sequencing. Second, a selectable marker conferring resistance to nourseothricin was introduced into Ethanol Red near the genomic location of interest. Part of this locus with the desired mutation was amplified together with the marker. The PCR product was then transformed into the corresponding mutants, which already has one copy of the target gene mutated and linked to hygromycin resistance marker. The selection of successful transformants was performed on double selection, and the mutants were first identified by PCR, then verified by Sanger sequencing.

Protocol Very-High Gravity (VHG) Fermentations

Lab-scale fermentations under VHG conditions were started with an overnight pre-growth of a single colony into 3 ml YPD, followed by transfer of the entire culture to 30 ml YP+4% (w/v) glucose and additional growth for 48 hours to the stationary phase (200 rpm, 30° C.); 250-ml Schott bottles each filled with 150 ml YP+35% (w/v) glucose and a magnetic rod (35×5 mm) were inoculated to a starting $OD_{600}$=1.0 (approximately $2.0\times10^7$ cells/ml). These bottles were sealed with a waterlock and stirred continuously at 150 rpm on a magnetic stirring platform (IKA® RO 15) at 30° C. The bottles were weighed daily to determine the cumulative weight loss, a proxy for $CO_2$ production and fermentations were stopped after 7 days. The ethanol production was determined using Anton Paar Alcolyzer. A Tukey HSD test was performed to check for significant differences in ethanol production between mutants and their respective controls.

REFERENCES

1. Steensels J., and K. J. Verstrepen (2014). Taming wild yeast: potential of conventional and nonconventional yeasts in industrial fermentations. *Annu. Rev. Microbiol.* 68:61-80.
2. Snoek T., M. Picca Nicolino, S. Van den Bremt, S. Mertens, and V. Saels et al. (2015). Large-scale robot-assisted genome shuffling yields industrial *Saccharomyces cerevisiae* yeasts with increased ethanol tolerance. *Biotechnology for Biofuels*, in press.
3. Mukherjee V., J. Steensels, B. Lievens, I. Van de Voorde, and A. Verplaetse et al. (2014). Phenotypic evaluation of natural and industrial *Saccharomyces* yeasts for different traits desirable in industrial bioethanol production. *Appl. Microbiol. Biotechnol.* 98:9483-9498.
4. Alexandre H., V. Ansanay-Galeote, S. Dequin, and B. Blondin (2001). Global gene expression during short-term ethanol stress in *Saccharomyces cerevisiae. FEBS Lett.* 498:98-103.
5. Fujita K., A. Matsuyama, Y. Kobayashi, and H. Iwahashi (2006). The genome-wide screening of yeast deletion mutants to identify the genes required for tolerance to ethanol and other alcohols. *FEMS Yeast Res.* 6:744-750.
6. Haft R. J., D. H. Keating, T. Schwaegler, M. S. Schwalbach, and J. Vinokur et al. (2014). Correcting direct effects of ethanol on translation and transcription machinery confers ethanol tolerance in bacteria. *Proc. Natl. Acad. Sci. U.S.A.* 111:E2576-2585.

Horinouchi T., K. Tamaoka, C. Furusawa, N. Ono, S. Suzuki et al. (2010). Transcriptome analysis of parallel-evolved *Escherichia coli* strains under ethanol stress. *BMC Genomics* 11:579.

8. Lewis J. A., A. T. Broman, J. Will, and A. P. Gasch (2014). Genetic architecture of ethanol-responsive transcriptome variation in *Saccharomyces cerevisiae* strains. *Genetics* 198:369-382.
9. Lewis J. A., I. M. Elkon, M. A. McGee, A. J. Higbee, and A. P. Gasch (2010). Exploiting natural variation in *Saccharomyces cerevisiae* to identify genes for increased ethanol resistance. *Genetics* 186:1197-1205.
10. van Voorst F., J. Houghton-Larsen, L. Jonson, M. C. Kielland-Brandt, and A. Brandt (2006). Genome-wide identification of genes required for growth of *Saccharomyces cerevisiae* under ethanol stress. *Yeast* 23:351-359.
11. Ehrenreich I. M., N. Torabi, Y. Jia, J. Kent, and S. Martis et al. (2010). Dissection of genetically complex traits with extremely large pools of yeast segregants. *Nature* 464:1039-1042.
12. Hu X. H., M. H. Wang, T. Tan, J. R. Li, and H. Yang et al. (2007). Genetic dissection of ethanol tolerance in the budding yeast *Saccharomyces cerevisiae. Genetics* 175:1479-1487.
13. Swinnen S., K. Schaerlaekens, T. Pais, J. Claesen, and G. Hubmann et al. (2012). Identification of novel causative genes determining the complex trait of high ethanol tolerance in yeast using pooled-segregant whole-genome sequence analysis. *Genome Res.* 22:975-984.
14. Wohlbach D. J., N. Rovinskiy, J. A. Lewis, M. Sardi, and W. S. Schackwitz et al. (2014). Comparative genomics of *Saccharomyces cerevisiae* natural isolates for bioenergy production. *Genome Biol. Evol.* 6:2557-2566.
15. D'Amore T., C. J. Panchal, I. Russell, and G. G. Stewart (1990). A study of ethanol tolerance in yeast. *Crit. Rev. Biotechnol.* 9:287-304.
16. Ding J., X. Huang, L. Zhang, N. Zhao, and D. Yang et al. (2009). Tolerance and stress response to ethanol in the yeast *Saccharomyces cerevisiae. Appl. Microbiol. Biotechnol.* 85:253-263.
17. Ma M., and Z. L. Liu (2010). Mechanisms of ethanol tolerance in *Saccharomyces cerevisiae. Appl. Microbiol. Biotechnol.* 87:829-845.
18. Avrahami-Moyal L., D. Engelberg, J. W. Wenger, G. Sherlock, and S. Braun (2012). Turbidostat culture of *Saccharomyces cerevisiae* W303-1A under selective pressure elicited by ethanol selects for mutations in SSD1 and UTH1. *FEMS Yeast Res.* 12:521-533.
19. Brown S. W., and S. G. Oliver (1982). Isolation of ethanol-tolerant mutants of yeast by continuous selection. *Eur. J. Appl. Microbiol. Biotechnol.* 16:119-122.
20. Goodarzi H., B. D. Bennett, S. Amini, M. L. Reaves, and A. K. Hottes et al. (2010). Regulatory and metabolic rewiring during laboratory evolution of ethanol tolerance in *E. coli. Mol. Syst. Biol.* 6:378.
21. Stanley D., S. Fraser, P. J. Chambers, P. Rogers, and G. A. Stanley (2010). Generation and characterisation of stable ethanol-tolerant mutants of *Saccharomyces cerevisiae. J. Ind. Microbiol. Biotechnol.* 37:139-149.
22. Cakar Z. P., U. O. Seker, C. Tamerler, M. Sonderegger, and U. Sauer (2005). Evolutionary engineering of multiple-stress resistant *Saccharomyces cerevisiae. FEMS Yeast Res.* 5:569-578.
23. Barrick J. E., D. S. Yu, S. H. Yoon, H. Jeong, and T. K. Oh et al. (2009). Genome evolution and adaptation in a long-term experiment with *Escherichia coli. Nature* 461:1243-1247.
24. Gresham D., M. M. Desai, C. M. Tucker, H. T. Jenq, and D. A. Pai et al. (2008). The repertoire and dynamics of evolutionary adaptations to controlled nutrient-limited environments in yeast. *PLoS Genet.* 4:e1000303.

25. Hong J., and D. Gresham (2014). Molecular specificity, convergence and constraint shape adaptive evolution in nutrient-poor environments. *PLoS Genet.* 10:e1004041.

26. Oz T., A. Guvenek, S. Yildiz, E. Karaboga, and Y. T. Tamer et al. (2014). Strength of selection pressure is an important parameter contributing to the complexity of antibiotic resistance evolution. *Mol. Biol. Evol.* 31:2387-2401.

27. Toprak E., A. Veres, J. B. Michel, R. Chait, and D. L. Hartl et al. (2011). Evolutionary paths to antibiotic resistance under dynamically sustained drug selection. *Nat. Genet.* 44:101-105.

28. Yona A. H., Y. S. Manor, R. H. Herbst, G. H. Romano, and A. Mitchell et al. (2012). Chromosomal duplication is a transient evolutionary solution to stress. *Proc. Natl. Acad. Sci. U.S.A.* 109:21010-21015.

29. Barrick J. E., and R. E. Lenski (2009). Genome-wide mutational diversity in an evolving population of *Escherichia coli. Cold Spring Harb. Symp. Quant. Biol.* 74:119-129.

30. Herron M. D., and M. Doebeli (2013). Parallel evolutionary dynamics of adaptive diversification in *Escherichia coli. PLoS Biol.* 11:e1001490.

31. Kvitek D. J., and G. Sherlock (2013). Whole genome, whole population sequencing reveals that loss of signaling networks is the major adaptive strategy in a constant environment. *PLoS Genet.* 9:e1003972.

32. Lang G. I., D. P. Rice, M. J. Hickman, E. Sodergren, and G. M. Weinstock et al. (2013). Pervasive genetic hitchhiking and clonal interference in forty evolving yeast populations. *Nature* 500:571-574.

33. Payen C., S. C. Di Rienzi, G. T. Ong, J. L. Pogachar, and J. C. Sanchez et al. (2014). The dynamics of diverse segmental amplifications in populations of *Saccharomyces cerevisiae* adapting to strong selection. *G*3 (Bethesda) 4:399-409.

34. Gerrish P. J., and R. E. Lenski (1998). The fate of competing beneficial mutations in an asexual population. *Genetica* 102-103:127-144.

35. Kao K. C., and G. Sherlock (2008). Molecular characterization of clonal interference during adaptive evolution in asexual populations of *Saccharomyces cerevisiae. Nat. Genet.* 40:1499-1504.

36. Gerstein A. C., H. J. Chun, A. Grant, and S. P. Otto (2006). Genomic convergence toward diploidy in *Saccharomyces cerevisiae. PLoS Genet.* 2:e145.

37. Kellis M., B. W. Birren, and E. S. Lander (2004). Proof and evolutionary analysis of ancient genome duplication in the yeast *Saccharomyces cerevisiae. Nature* 428:617-624.

38. Wolfe K. H., and D. C. Shields (1997). Molecular evidence for an ancient duplication of the entire yeast genome. *Nature* 387:708-713.

39. Fawcett J. A., S. Maere, and Y. Van de Peer (2009). Plants with double genomes might have had a better chance to survive the Cretaceous-Tertiary extinction event. *Proc. Natl. Acad. Sci. U.S.A.* 106:5737-5742.

40. Selmecki A. M., Y. E. Maruvka, P. A. Richmond, M. Guillet, and N. Shoresh et al. (2015). Polyploidy can drive rapid adaptation in yeast. *Nature* 519:349-352.

41. Galitski T., A. J. Saldanha, C. A. Styles, E. S. Lander, and G. R. Fink (1999). Ploidy regulation of gene expression. *Science* 285:251-254.

42. Ohno S. (1970) Evolution by gene duplication. Berlin: Springer-Verlag.

43. Semon M., and K. H. Wolfe (2007). Consequences of genome duplication. *Curr. Opin. Genet. Dev.* 17:505-512.

44. Andalis A. A., Z. Storchova, C. Styles, T. Galitski, and D. Pellman et al. (2004) Defects arising from whole-genome duplications in *Saccharomyces cerevisiae. Genetics* 167:1109-1121.

45. Song K., P. Lu, K. Tang, and T. C. Osborn (1995). Rapid genome change in synthetic polyploids of *Brassica* and its implications for polyploid evolution. *Proc. Natl. Acad. Sci. U.S.A.* 92:7719-7723.

46. Storchova Z., A. Breneman, J. Cande, J. Dunn, and K. Burbank et al. (2006). Genome-wide genetic analysis of polyploidy in yeast. *Nature* 443:541-547.

47. Anderson J. B., C. Sirjusingh, and N. Ricker (2004). Haploidy, diploidy and evolution of antifungal drug resistance in *Saccharomyces cerevisiae. Genetics* 168:1915-1923.

48. Gerstein A. C., L. A. Cleathero, M. A. Mandegar, and S. P. Otto (2011). Haploids adapt faster than diploids across a range of environments. *J. Evol. Biol.* 24:531-540.

49. Zeyl C., T. Vanderford, and M. Carter (2003). An evolutionary advantage of haploidy in large yeast populations. *Science* 299:555-558.

50. Lynch M., W. Sung, K. Morris, N. Coffey, and C. R. Landry et al. (2008). A genome-wide view of the spectrum of spontaneous mutations in yeast. *Proc. Natl. Acad. Sci. U.S.A.* 105:9272-9277.

51. Giraud A., I. Matic, O. Tenaillon, A. Clara, and M. Radman et al. (2001). Costs and benefits of high mutation rates: adaptive evolution of bacteria in the mouse gut. *Science* 291:2606-2608.

52. McDonald M. J., Y. Y. Hsieh, Y. H. Yu, S. L. Chang, and J. Y. Leu (2012). The evolution of low mutation rates in experimental mutator populations of *Saccharomyces cerevisiae. Curr. Biol.* 22:1235-1240.

53. Pal C., M. D. Macia, A. Oliver, I. Schachar, and A. Buckling (2007). Coevolution with viruses drives the evolution of bacterial mutation rates. *Nature* 450:1079-1081.

54. Sniegowski P. D., P. J. Gerrish, and R. E. Lenski (1997). Evolution of high mutation rates in experimental populations of *E. coli. Nature* 387:703-705.

55. Drotschmann K., A. B. Clark, H. T. Tran, M. A. Resnick, and D. A. Gordenin et al. (1999). Mutator phenotypes of yeast strains heterozygous for mutations in the MSH2 gene. *Proc. Natl. Acad. Sci. U.S.A.* 96:2970-2975.

56. Lang G. I., L. Parsons, and A. E. Gammie (2013). Mutation rates, spectra, and genome-wide distribution of spontaneous mutations in mismatch repair deficient yeast. *G*3 (Bethesda) 3:1453-1465.

57. Huang da W., B. T. Sherman, and R. A. Lempicki (2009). Systematic and integrative analysis of large gene lists using DAVID bioinformatics resources. *Nat. Protoc.* 4:44-57.

58. De Maeyer D., J. Renkens, L. Cloots, L. De Raedt, and K. Marchal (2013). PheNetic: network-based interpretation of unstructured gene lists in *E. coli. Mol. Biosyst.* 9:1594-1603.

59. De Maeyer D., B. Weytjens, J. Renkens, L. De Raedt, and K. Marchal (2015). PheNetic: networkbased interpretation of molecular profiling data. *Nucleic Acids Res.*

60. Kubota S., I. Takeo, K. Kume, M. Kanai, and A. Shitamukai et al. (2004). Effect of ethanol on cell growth of budding yeast: genes that are important for cell growth in the presence of ethanol. *Biosci. Biotechnol. Biochem.* 68:968-972.

61. Gasch A. P., P. T. Spellman, C. M. Kao, O. Carmel-Harel, and M. B. Eisen et al. (2000). Genomic expression programs in the response of yeast cells to environmental changes. *Mol. Biol. Cell.* 11:4241-4257.
62. Lu C., M. J. Brauer, and D. Botstein (2009). Slow growth induces heat-shock resistance in normal and respiratory-deficient yeast. *Mol. Biol. Cell.* 20:891-903.
63. Brauer M. J., C. Huttenhower, E. M. Airoldi, R. Rosenstein, and J. C. Matese et al. (2008). Coordination of growth rate, cell cycle, stress response, and metabolic activity in yeast. *Mol. Biol. Cell.* 19:352-367.
64. DeLuna A., K. Vetsigian, N. Shoresh, M. Hegreness, and M. Colon-Gonzalez et al. (2008). Exposing the fitness contribution of duplicated genes. *Nat. Genet.* 40:676-681.
65. Bonangelino C. J., E. M. Chavez, and J. S. Bonifacino (2002). Genomic screen for vacuolar protein sorting genes in *Saccharomyces cerevisiae. Mol. Biol. Cell.* 13:2486-2501.
66. Duitama J., A. Sanchez-Rodriguez, A. Goovaerts, S. Pulido-Tamayo, and G. Hubmann et al. (2014). Improved linkage analysis of Quantitative Trait Loci using bulk segregants unveils a novel determinant of high ethanol tolerance in yeast. *BMC Genomics* 15:207.
67. Teixeira M. C., L. R. Raposo, N. P. Mira, A. B. Lourenco, and I. Sa-Correia (2009). Genome-wide identification of *Saccharomyces cerevisiae* genes required for maximal tolerance to ethanol. *Appl. Environ. Microbiol.* 75:5761-5772.
68. Steensels J., T. Snoek, E. Meersman, M. P. Nicolino, and K. Voordeckers et al. (2014). Improving industrial yeast strains: exploiting natural and artificial diversity. *FEMS Microbiol. Rev.* 38:947-995.
69. Dunham M. J., H. Badrane, T. Ferea, J. Adams, and P. O. Brown et al. (2002). Characteristic genome rearrangements in experimental evolution of *Saccharomyces cerevisiae. Proc. Natl. Acad. Sci. U.S.A.* 99:16144-16149.
70. Rancati G., N. Pavelka, B. Fleharty, A. Noll, and R. Trimble et al. (2008). Aneuploidy underlies rapid adaptive evolution of yeast cells deprived of a conserved cytokinesis motor. *Cell* 135:879-893.
71. Wildenberg G. A., and A. W. Murray (2014). Evolving a 24-hour oscillator in budding yeast. *Elife* 3.
72. Gerstein A. C., and S. P. Otto (2012). Cryptic fitness advantage: diploids invade haploid populations despite lacking any apparent advantage as measured by standard fitness assays. *PLoS One* 6:e26599.
73. Wu C. Y., P. A. Rolfe, D. K. Gifford, and G. R. Fink (2010). Control of transcription by cell size. *PLoS Biol.* 8:e1000523.
74. Zorgo E., K. Chwialkowska, A. B. Gjuvsland, E. Garre, and P. Sunnerhagen et al. (2013). Ancient evolutionary trade-offs between yeast ploidy states. *PLoS Genet.* 9:e1003388.
75. Pavelka N., G. Rancati, J. Zhu, W. D. Bradford, and A. Saraf et al. (2010). Aneuploidy confers quantitative proteome changes and phenotypic variation in budding yeast. *Nature* 468:321-325.
76. Torres E. M., T. Sokolsky, C. M. Tucker, L. Y. Chan, and M. Boselli et al. (2007). Effects of aneuploidy on cellular physiology and cell division in haploid yeast. *Science* 317:916-924.
77. Sunshine A. B., C. Payen, G. T. Ong, I. Liachko, and K. M. Tan et al. (2015). The fitness consequences of aneuploidy are driven by condition-dependent gene effects. *PLoS Biol.* 13:e1002155.
78. Pavelka N., G. Rancati, and R. Li (2010). Dr. Jekyll and Mr. Hyde: role of aneuploidy in cellular adaptation and cancer. *Curr. Opin. Cell. Biol.* 22:809-815.
79. Sheltzer J. M., and A. Amon (2011). The aneuploidy paradox: costs and benefits of an incorrect karyotype. *Trends Genet.* 27:446-453.
80. Sheltzer J. M., H. M. Blank, S. J. Pfau, Y. Tange, and B. M. George et al. (2011). Aneuploidy drives genomic instability in yeast. *Science* 333:1026-1030.
81. Koschwanez J. H., K. R. Foster, and A. W. Murray (2011). Sucrose utilization in budding yeast as a model for the origin of undifferentiated multicellularity. *PLoS Biol.* 9:e1001122.
82. Wenger J. W., J. Piotrowski, S. Nagarajan, K. Chiotti, and G. Sherlock et al. (2011). Hunger artists: yeast adapted to carbon limitation show trade-offs under carbon sufficiency. *PLoS Genet.* 7:e1002202.
83. Ihmels J., S. Bergmann, M. Gerami-Nejad, I. Yanai, and M. McClellan et al. (2005). Rewiring of the yeast transcriptional network through the evolution of motif usage. *Science* 309:938-940.
84. Rozpedowska E., L. Hellborg, O. P. Ishchuk, F. Orhan, and S. Galafassi et al. (2011). Parallel evolution of the make-accumulate-consume strategy in *Saccharomyces* and *Dekkera* yeasts. *Nat. Commun.* 2:302.
85. Thomson J. M., E. A. Gaucher, M. F. Burgan, D. W. De Kee, and T. Li et al. (2005). Resurrecting ancestral alcohol dehydrogenases from yeast. *Nat. Genet.* 37:630-635.
86. Brachmann C. B., A. Davies, G. J. Cost, E. Caputo, and J. Li et al. (1998). Designer deletion strains derived from *Saccharomyces cerevisiae* S288C: a useful set of strains and plasmids for PCR-mediated gene disruption and other applications. *Yeast* 14:115-132.
87. Guldener U., S. Heck, T. Fielder, J. Beinhauer, and J. H. Hegemann (1996). A new efficient gene disruption cassette for repeated use in budding yeast. *Nucleic Acids Res.* 24:2519-2524.
88. Gueldener U., J. Heinisch, G. J. Koehler, D. Voss, and J. H. Hegemann (2002). A second set of loxP marker cassettes for Cre-mediated multiple gene knockouts in budding yeast. *Nucleic Acids Res.* 30: e23.
89. Li H., and R. Durbin (2009). Fast and accurate short read alignment with Burrows-Wheeler transform. *Bioinformatics* 25:1754-1760.
90. DePristo M. A., E. Banks, R. Poplin, K. V. Garimella, and J. R. Maguire et al. (2011). A framework for variation discovery and genotyping using next-generation DNA sequencing data. *Nat. Genet.* 43:491-498.
91. Cingolani P., A. Platts, le L. Wang, M. Coon, and T. Nguyen et al. (2012). A program for annotating and predicting the effects of single nucleotide polymorphisms, SnpEff: SNPs in the genome of *Drosophila melanogaster* strain w1118; iso-2; iso-3. *Fly* (*Austin*) 6:80-92.
92. Huang da W., B. T. Sherman, and R. A. Lempicki (2009). Bioinformatics enrichment tools: paths toward the comprehensive functional analysis of large gene lists. *Nucleic Acids Res.* 37:1-13.
93. Kanehisa M., and S. Goto (2000). KEGG: kyoto encyclopedia of genes and genomes. *Nucleic Acids Res.* 28:27-30.
94. Jensen L. J., M. Kuhn, M. Stark, S. Chaffron, and C. Creevey et al. (2009). STRING 8—a global view on proteins and their functional interactions in 630 organisms. *Nucleic Acids Res.* 37:D412-416.
95. Teixeira M. C., P. Monteiro, P. Jain, S. Tenreiro, and A. R. Fernandes et al. (2006). The YEASTRACT® database: a tool for the analysis of transcription regulatory associations in *Saccharomyces cerevisiae. Nucleic Acids Res.* 34:D446-451.

96. Maere S., K. Heymans, and M. Kuiper (2005). BiNGO: a Cytoscape plugin to assess overrepresentation of gene ontology categories in biological networks. *Bioinformatics* 21:3448-3449.

97. Casey G. P., and W. M. Ingledew (1986). Ethanol tolerance in yeasts. *Crit. Rev. Microbiol.* 13(3):219-80. Review.

98. D'Amore, T. and G. G. Stewart (1987). Ethanol tolerance of yeast. *Enzyme Microb. Technol.* 9:322-330.

99. Carlsen H. N., H. Degn, and D. Lloyd (1991). Effects of alcohols on the respiration and fermentation of aerated suspensions of baker's yeast. *J. Gen. Microbiol.* December; 137(12):2879-83.

100. Casal M., H. Cardoso, and C. Ledo (1998). Effects of ethanol and other alkanols on transport of acetic acid in *Saccharomyces cerevisiae. Appl. Environ. Microbiol.* February; 64(2):665-8.

The invention claimed is:

1. A genetically modified *Saccharomyces* spp. comprising a MEX67 allele having a G to A mutation at a position relative to position 456 of SEQ ID NO: 1.

2. The *Saccharomyces* spp. of claim 1 further comprising one or more additional alcohol tolerance alleles and/or accumulation modulating alleles.

3. The *Saccharomyces* spp. of claim 2, wherein the one or more additional alcohol tolerance alleles and/or accumulation modulating alleles are selected from the group consisting of PCA1, PRT1, YBL059W, HEM13, HST4, and VPS70.

4. The *Saccharomyces* spp. of claim 2, wherein the additional alcohol tolerance allele(s) and/or accumulation modulating allele(s) are selected from the group consisting of PRT1 with a A to G mutation at a position relative to position 1384 of SEQ ID NO: 3, YBL059W with a G to T mutation at a position relative to position 479 of SEQ ID NO: 4, HEM13 with a G to C mutation at a position relative to position 700 of SEQ ID NO: 5, HST4 with a G to C mutation at a position relative to position 262 of SEQ ID NO: 6, and VPS70 with a C to A mutation at a position relative to position 595 of SEQ ID NO: 7.

5. The *Saccharomyces* spp. of claim 1, wherein the *Saccharomyces* spp. is *Saccharomyces cerevisiae*.

6. The *Saccharomyces* spp. of claim 1, wherein the MEX67 allele is SEQ ID NO: 1 with a G456A mutation.

* * * * *

SEQUENCE LISTING

<160> NUMBER OF SEQ ID NOS: 7

<210> SEQ ID NO 1
<211> LENGTH: 1800
<212> TYPE: DNA
<213> ORGANISM: Saccharomyces cerevisiae

<400> SEQUENCE: 1
atgagcggat ttcacaatgt tggaaatatc aatatgatgg ctcaacagca gatgcaacaa 60
aatagaataa agattagcgt gaggaactgg cagaatgcaa ccatgaacga tttgattaat 120
tttataagcc gcaacgctcg agtagctgtt tttgacgctc atgtggaagg acctttagtt 180
attggatatg tcaactcaaa ggcagaagca gaatcgttaa tgaaatggaa cggtgtccgg 240
tttgcaggca gtaatttaaa gttcgaactt ttagataaca atggggcctc tgcgggaact 300
tcagacacca tttcgttctt gagggggggtg ctccttaaga ggtatgaccc acaaacaaaa 360
ttactaaatt tgggcgcttt acattcagat cccgagttaa ttcaaaaggg cgtctttagt 420
tccatctcca cccagtctaa gatgtttcca gcaatgatga aactggcttc tacagaaaaa 480
agtttgatag tggaaagtgt caatcttgct gacaaccaac ttaaggacat ctcagcaatt 540
tccacattgg ctcaaacatt tcctaatttg aaaaacctct gtctggccaa caatcagatt 600
tttagattta gatcgctaga agtttggaag aacaaattca aagatctaag agagcttttg 660
atgacaaata acccgataac caccgataag ttgtatcgca ctgaaatgtt aagattattt 720
ccgaaattgg ttgtactaga taacgtgatt gtgagagacg aacaaaaatt gcaaagcgtt 780
tactcattac cgatgaagat tcaacagttt tttttcgaaa acgatgcatt agggcaatca 840
tctacagact ttgcaactaa ctttttgaat ctatgggaca ataatagaga acagctgtta 900
aatttgtatt cgccccaatc ccagttttct gtttccgtgg attctactat tcctccatct 960
acggtaacag attcggacca aactccagca tttggttatt acatgtcgtc ctcacgtaat 1020
atatccaaag tgtccagtga aaaatctatc cagcagagat tgtcaatcgg acaagagtcc 1080
attaatagta tattcaagac tttgccgaaa acaaagcacc atttacaaga acaacccaat 1140
gaatactcaa tggaaacaat tagttatcct caaataaatg ggttcgttat tacgttgcac 1200 gggtttttg aagagactgg caagcctgaa ctggaatcca ataaaaaaac ggggaaaaat 1260
aactatcaaa agaatagaag atacaatcat ggttacaact ccacatcaaa taataagtta 1320
tccaaaaaat cctttgatag aacctgggta attgttccaa tgaataatag tgtcataatc 1380
gcatctgatc tgttaactgt aagagcgtat tccacaggcg cttggaaaac tgcatctatt 1440
gcaatagcac agcctccaca gcaacaggcc tcggtcctac cacaggtcgc aagcatgaac 1500
ccaaatataa cgacaccacc gcagccacaa ccttcagtgg taccaggagg gatgagcatt 1560
cccggtgcac cccaaggagc catggtcatg gcgcccactt tgcaactacc tccagatgtc 1620
cagtcgcggc taaatcccgt acaactcgag ctgctgaata aactacattt ggaaacgaaa 1680
ttgaatgcag aatacacgtt catgttggcc gagcaaagta actggaacta tgaagttgcc 1740

-continued ataaaaggtt ttcagagtag catgaatggc atccctagag aagcatttgt gcagttctaa 1800

<210> SEQ ID NO 2
<211> LENGTH: 3752
<212> TYPE: DNA
<213> ORGANISM: Saccharomyces cerevisiae

<400> SEQUENCE: 2
atgaagccgg aaaaactctt ctccggttta ggtaccagcg atggcgagta tggagtggta 60
aatagcgaga acatatcaat agatgctatg caagataata gaggcgagtg tcatcgtagg 120
tccatagaaa tgcatgctaa tgacaatctg ggattggtct cccagcgaga ctgtaccaat 180
cggcccaaaa ttactcctca ggaatgtttg agtgagactg agcagatatg ccatcatggc 240
gagaatagga ctaaggctgg gttagatgta gacgatgctg aaaccggtgg tgaccacacc 300
aatgaatccc gtgtagatga atgttgtgct gagaagacac tgagactggc ttggatgtgg 360
acagctgttg cggcgatgct caaaccggtg gagaccacac caatgaatcc tgtgcagatg 420
aatgttgtgc taagaaagcg aacgacactg agactggctt ggatgtggac agctgttgcg 480
gcgatgctca aaccggtgga gaccacacca atgaatcctg tgttgatgaa tgctgcgtta 540
gagattcttc agtgatggtc gaggaaggta caggcagctg cgaagctgta tcttctaaag 600
aacaattgct gaccagcttt gaagttgttc caggcaaatc tgaaggtctg caatctattc 660
atgatattag agagacaact cgctgcaata ccaattccaa ccaacacaca gggaagggta 720
ggctttgcct tgaatccagt gactctacac tcaagaaaag acgttgtaaa gttagcagac 780
agaaaattga agtttccagt aagcctgagt gctgcaacat ttcatgtgtt gagcggattg 840
catctcgtag ctgtgaaaag aggactttta aaggtaccac caatgttgga atttctggga 900
gtagctctac cgacagttta agcgagaagt tcttcagcga acagtactct agaatgtaca 960
atcgttactc ctcaatttg aaaaatttag gttgtatctg taactatttg cgtactttgg 1020
gaaaggaatc ttattgtctc ccaaaggtgc gtttttgtag cggggagggt gcttctaaaa 1080
agacaaaata ctcctaccgc aacagttctg gatgtttaac aaagaaaaag acctatggag 1140
acaaagaaag gttgagcaat gacaatggcc atgctgattt tgtttgttct aaaagttgtt 1200
gcactaaaat gaaggattgt gctgttactt caactatttc tggacactct tcgagtgaaa 1260
tttcaagaat cgtatcaatg gaaccaattg gaaatcatct taatcttgag gcaggatcta 1320
ccgctactga gcacattgtt cttagtgttt caggaatgac ctgtactggt tgtgaaacaa 1380
aacttaagaa atcatttggc gcgctcaaat gtgttcacgg tttgaagacc agtttaatat 1440
tatcgcaagc tgaatttaat ctggatcttg ctcagggatc tgtcaaggac gttatcaagc 1500
acttgagcaa aactactgaa ttcaagtacg aacagatttc aaatcatgct tcaactatag 1560
atgttgttgc tccttatgca gcaaaagatt ttattaatga ggaatggcca caaggtgtca 1620
cagagctgaa aattgttgag agaaatgtca ttcgtattta ctttgaccca aaggttatag 1680
gtgccagaga tcttgtcaat gaaggatgga gcgtgcctgt tagtattgct ccattcagtt 1740
gtcatccaac cattgaagtg ggaaggaagc atttagttcg tgtaggctgc acgaccgctt 1800
tatccataat attgacgatc ccgattctcg tgatggcttg ggctccacag cttcgtgaaa 1860
aaatttcaac tatgtccgtg tcaatggtgc tagcaactat tatccaattt gttattgcag 1920
gaccgtttta cttaaatgcc ttgaagagtt tgatattttc caggctcatt gaaatggatc 1980
tactaatagt tttaagcact agcgctgcct acatattttc gattgtatca tttggatatt 2040

-continued

```
tcgttgctgg acacccgtta tctacggagc agttttttga gaccagctct ttgcttataa   2100

ctctcatcat ggttggtcgc tttgtgagtg aattagctag acatagggct gtaaagtcaa   2160

tatcagtacg ttctttacag gcctcttctg ctattctggt agataaaact ggtaaagaga   2220

cggaaattga tattagactt ctccaatatg gcgatatttt taagatttta cctgattcaa   2280

gaatcccgac tgatggaaca gtcatttctg ggtcttctga agtcgacgaa gcgttaatca   2340

caggtgaatc tatgccagtc ccgaaaaagt gtcaatcaat tgttgttgca ggatcggtaa   2400

atggcactgg taccttgttt gtaaagctga gcaagcttcc agggaacaat actattagta   2460

ccatagccac gatggtcgat gaagcaaaat taactaagcc aaagatccaa aatatcgctg   2520

ataaaattgc aagttatttc gtgccaacta tcattggaat cactgtcgtc accttttgcg   2580

tttggatagc ggttggaatc cgtgtgcaaa agcaatcccg ctccgatgcc gtaattcagg   2640

ccattatata tgccattacg gtacttatcg tgtcatgtcc ctgcgcgatt ggacttgccg   2700

ttcctatcgt atttgttatt gcaagtggcg tcgctgcgaa aagaggggta atcttcaaat   2760

cagcagagag tatagaagtt gctcacaaca cttcgcatgt tgtcttcgat aaaacgggta   2820

ccctaactga aggaaaactt actgtagtac atgaaactgt taggggtgat cgtcataatt   2880

ctcaatcttt gttgcttgga ttaactgaag gaataaaaca cccagtttcc atggcaatag   2940

catcatatct caaagaaaaa ggtgtttctg ctcaaaatgt ttctaataca aaagctgtga   3000

ctggtaaggg ggtagaagga acatcatact ctggtttgaa gttacaagga ggaaactgtc   3060

gttggcttgg tcataacaat gatcctgacg ttcgaaaagc ccttgaacaa ggatattctg   3120

tgttctgttt tagtgttaat ggttcagtca ctgcagttta tgcattagag gactctttac   3180

gggcagatgc tgtctccact attaacttgt tacgccaaag agggatttca ctacacattt   3240

tatcagggga tgacgatgga gccgttcgtt ctatggcagc ccgtcttgga attgaaagct   3300

ccaatattcg ttctcacgca acgcctgcag aaaagagtga atatattaag gatattgtcg   3360

aaggaagaaa ttgcgatagt tcttcgcagt caaaaagacc ggttgttgtt ttttgcggtg   3420

acggaacaaa cgacgcaatt gctttgactc aagcaacgat tggagttcat atcaatgagg   3480

gaagtgaggt tgccaagcta gctgctgatg tagttatgtt aaagccaaag ctcaacaata   3540

ttttgaccat gataactgta agtcaaaagg ccatgtttag ggtcaaattg aatttcttat   3600

ggagttttac ttacaactta tttgctatcc ttttggcggc tggtgccttt gttgactttc   3660

atattccacc agagtatgcg ggtttagggg aactagttag tatcctccct gtaatttttg   3720

tagctacact tctgcgttat gcaaagattt ag                                  3752
```

<210> SEQ ID NO 3
<211> LENGTH: 2298
<212> TYPE: DNA
<213> ORGANISM: Saccharomyces cerevisiae

<400> SEQUENCE: 3

```
atgaaaaatt ttcttccacg cacattgaaa aatatttacg aattatattt caataacatc     60

tcagtacata gtaaagtatc tcgcaacaca cagctcaaaa ggtcaaagat aattcaaatg    120

actaccgaga ctttcgaaga cattaagcta gaggacatcc ctgttgacga cattgatttt    180

tccgacctgg aagaacaata caaggtcact gaagaattca atttcgatca gtacatcgtc    240

gttaatggtg ccccagtcat cccatccgcc aaagttcctg ttttgaaaaa ggctttgact    300

tctttgtttt ccaaagctgg taaagttgtt aacatggaat ttccaattga tgaagctact    360

ggtaagacga aaggttttct cttcgtggaa tgtggctcaa tgaacgatgc taaaaaaatt    420
```

-continued atcaagagtt tccacggtaa aagactggat ttaaaacatc gtttgtttct ttatactatg 480
aaagatgttg aaagatataa ttctgacgaa tttgacaccg aattcaggga gcctgatatg 540
cctacattcg ttccatctag ttccttaaaa tcctggttaa tggacgacaa agtgagagat 600
cagtttgtat tacaagatga cgtgaagact agtgtgttct ggaactctat gttcaatgaa 660
gaagattctt tggtggaatc tagagagaac tggtctacca attatgttag attctcccca 720
aagggtacct atttgtttc ttaccatcaa cagggtgtaa ctgcatgggg tggtccaaac 780
ttcgatcgtt tgagaagatt ctatcatcca gatgtaagaa actcttccgt ctctccgaat 840
gaaaagtacc tggtcacttt ctccacggaa ccaatcattg tagaagaaga taacgaattc 900
tctccattta ccaagaaaaa tgagggccat caattatgca tctgggacat tgcttctggt 960
ctgttgatgg caactttccc agtgataaag agcccatatc tgaaatggcc tttagttaga 1020
tggtcttata atgataaata ttgtgcccgt atggttggag acagtttaat agttcacgat 1080
gctactaaaa acttcatgcc attagaagct aaggctttga agccttctgg tattagagat 1140
ttctcatttg ctccagaagg tgttaaatta caaccattca gaaacggtga cgagccttct 1200
gttttattgg cttattggac tcccgagact aataattccg cttgtactgc taccattgct 1260
gaagttcctc gcggtagagt gctaaaaacc gttaacttag ttcaagtctc caacgtaact 1320
ctgcactggc aaaaccaagc tgagttcctg tgcttcaatg tcgaacgtca cacaaagtct 1380
ggtaagactc aattcagtaa tctacaaatt tgtaggttga ctgaaagaga tataccagtt 1440
gaaaaggttg aattgaaaga tagtgtcttt gaattcggtt gggaacccca cggaaacaga 1500
tttgttacaa tttctgttca tgaagtagct gatatgaatt atgctatccc agcaaataca 1560
atcagatttt acgctccaga aactaaagaa aagactgcta agaacgtaat taaaagatgg 1620
agcttggtca aagaaattcc aaaaactttt gccaacactg tttcttggtc cccagcaggt 1680
agatttgtgg ttgtaggtgc tttagtgggt ccaaacatgc gtagatcaga cctacaattt 1740
tacgatatgg actatccagg tgaaaagaat attaatgaca ataatgatgt ttcagcttct 1800
ttgaaagatg ttgctcatcc tacctactct gcggctacta atatcacttg ggatccatct 1860
ggtagatacg ttaccgcatg gtcaagttct ttgaaacaca aggtggagca tggttacaaa 1920
attttcaata ttgctggtaa cttagttaaa gaagacatca ttgctggctt caagaacttt 1980
gcctggagac caaggccagc ttccattttg cctaacgccg aaaggaaaaa ggttaggaaa 2040
aacttgaggg aatggtctgc ccaattcgaa gagcaagatg caatggaagc tgacaccgcc 2100
atgagagatt tgattctaca ccaacgtgaa ttattgaagc aatggaccga atatagagaa 2160
aaaattggcc aagaaatgga aaaatctatg aatttcaaaa tctttgatgt tcaaccagaa 2220
gatgccagcg atgactttac caccatcgaa gagatagttg aagaagtttt ggaagaaaca 2280
aaggaaaagg tcgaataa 2298

<210> SEQ ID NO 4
<211> LENGTH: 651
<212> TYPE: DNA
<213> ORGANISM: Saccharomyces cerevisiae

<400> SEQUENCE: 4
atgttattgg acgcgcagcg attttttaat aggtctttct ctattaatgt aatatgcgaa 60
ttgaaacata atgtaaacac aagaagaaaa ttcgaaataa aggactggcc aacaataatg 120
ttagtgaaca gaaacgacaa gcccaaaatc agcagtgagg aagtcacaca ttttatagac 180

-continued

```
gactataaaa agaggaggaa aactcagatg acacgattct tcggaatcac tatttttaca    240

cttataacat gtagaattgc catgaagaaa atgataactg caaaaggtat gcataggcaa    300

taacttcggc ctcatactca aagaacacgt ttactaacat aacttattta catagtgcca    360

ttgaacactt ttcaagcaaa ctacgccagc cggacgcaga caataacaca cacacaaaag    420

agtcttgcag gttctctttt agcggcaacg ggcatgacac taggtatatt tggtatgggc    480

atcacaggga catgttggag ctgggatgtt tcatcatttc aggaactaaa gcaacgtctg    540

gaaaggcgtg ccaacaacga atttgtagtg acaaacatgc ctctggataa aagaagccag    600

caagtagtgg acagcttagt taagacacac aattcatctc tttgtaaata g             651
```

<210> SEQ ID NO 5
<211> LENGTH: 987
<212> TYPE: DNA
<213> ORGANISM: Saccharomyces cerevisiae

<400> SEQUENCE: 5

```
atgcctgccc ctcaagatcc aaggaatctt ccaattagac aacaaatgga agctcttatc     60

cgtcgcaaac aagctgaaat cacgcaaggt ttggaatcca tcgatactgt taagttccac    120

gctgatactt ggacccgtgg taacgatggt ggtggtggta cctctatggt tatccaagac    180

ggtacaactt tcgaaaaagg tggtgttaat gtctccgttg tttatggtca attgagccca    240

gcggccgttt cagccatgaa agctgatcat aagaatctgc gtctaccaga agatccaaag    300

actggtttgc cagttaccga cggtgtcaag ttcttcgctt gtggtttaag tatggtcatt    360

catcccgtta acccacacgc tccaaccaca cacttaaact accgttactt cgaaacttgg    420

aaccaagatg gcaccccaca aacttggtgg tttggtggtg gtgctgattt gacaccttct    480

tacttatacg aagaagacgg tcaattattc caccaactgc acaaggatgc cttggacaag    540

cacgacactg ctttgtaccc acgtttcaag aaatggtgtg atgagtactt ctacattact    600

caccgtaagg aaacacgtgg tattggtggt atattctttg acgattatga tgaacgtgac    660

ccacaagaaa tattgaagat ggttgaagac tgtttcgatg ctttcttgcc atcctacttg    720

actatcgtca agagaagaaa agatatgcca tatacaaagg aagaacaaca atggcaggcc    780

attagacgtg gtagatacgt tgaattcaac ttaatctacg atagaggtac ccaattcggt    840

ttgagaaccc caggctctag agttgagtca attttgatga gtttgcctga acatgcttca    900

tggttataca accatcaccc tgctcctggt tccagagaag ctaaattact agaagttacc    960

accaaaccaa gagagtgggt taaataa                                        987
```

<210> SEQ ID NO 6
<211> LENGTH: 1113
<212> TYPE: DNA
<213> ORGANISM: Saccharomyces cerevisiae

<400> SEQUENCE: 6

```
atgaagcaaa aatttgtact accgatcacc ccaccaagta cggtggaaaa gaagcctcaa     60

acagaaaacc gttgcaatga gaatttgaag cctagaagat tgctaccgca attaaaaaga    120

agtgtccgca acaggaaacc tagactgtca tataggcctg agttaaactc tgtgtttgat    180

ctggatgcgt acgtggattc gacacacttg tccaaatccc aacgccatca tatggaccgt    240

gacgccggtt ttattagcta tgctctgaat tatagcaaaa gaatggttgt agtcagcggg    300

gcaggtatat ctgttgccgc tggtataccg gattttagat ccagtgaagg gattttctct    360

actgtgaacg gcggctctgg gaaagatttg tttgactaca atcgtgtgta tggcgacgaa    420
```

-continued tcaatgagtt tgaaatttaa tcagttaatg gtgtcattgt tcagattatc caagaattgc 480
caacctacaa aatttcatga aatgctcaat gagtttgcta gggatggcag gctattgaga 540
ctgtacacgc agaatattga cggtttagat acacaattac ctcatttatc aactaatgtg 600
cctctggcga agccaatacc cagtacagta caattacacg gaagcataaa acacatggaa 660
tgcaataaat gtctgaatat caaacctttt gaccctgaac tgttcaaatg cgacgacaaa 720
tttgattctc ggactgaaat cataccgtca tgtccacaat gtgaagaata tgaaacagtt 780 agaaaaaattg caggcttaag atctactggt gtgggcaagt tgcgtccaag agtaatttta 840
tacaatgagg tccaccctga aggtgatttt atcggtgaaa ttgccaataa tgacttaaag 900
aaaagaattg attgtttgat tattgttgga acgagtttga agattcccgg agtgaaaaat 960
atttgcaggc agtttgcggc caaagtccat gcaaacaggg gtattgtgtt atatttaaac 1020
accagtatgc cgcctaagaa tgtgctagac tctttgaaat ttgtagacct agttgtactg 1080
ggagattgtc agcatgttac ctcattatta tag 1113

<210> SEQ ID NO 7
<211> LENGTH: 2436
<212> TYPE: DNA
<213> ORGANISM: Saccharomyces cerevisiae

<400> SEQUENCE: 7
atgagaatga tacagagaga gagaaagaga gagaaagagg aaggtcaatt aaaggagaga 60
actgttgtta atatggcaga ccctgatgac aatgaggccg aagccactgg attacaacaa 120
tatagtggcg agaccactcg cgatgacaat gaagaaagca tgaatgattc tttcacttta 180
acatccagga atagaggcag aagtaataca atatctagta ttgttagtgg ttatgaaata 240
atgaaagaac atatggacag ggaaaagttt atgtacttga ttctagcgag tctccttttg 300
tacatgggat ttgttgccgc atttgctccc aggacgtctt tatcaagaga ctttcggcgg 360
tttcactctt ccagattgac gaatgcagag gtttatagga tatacttgaa ctccttgcaa 420
caggaaaata gagcgaaaga acatgtatac aagtatgctg ggtacatgag caacggagca 480
agtgattcgt caacgtttaa atataccttg gacgagtttc tagatatggg gtacaaaccc 540
aaagttgaaa aatattaccc atggataggt gaaccagtag acactaacgt agctctttta 600
gaaaatggta aagtggtcta cgaagcaagc atgatcgagg atagagttaa aggtgatcct 660
gcttctcacg ctaggaagag gcaaaagggt ttccatcaat attcaaaaaa tggaagtgta 720
actgctcgat acgtgttttg caattatggt agcatcggtg actacaagct actttttgaag 780 aaaaacattg atattgaaga taaaatccac atcgtacgat cgggtaaaat actacctgga 840
ttaaaggtaa agaatgcaga actttatggc gcttccagtg tcattatata tacagaccca 900
tttgacgatg gtaaagttac tgaggaaaat gggtttttac actatcctta tggaccagca 960
agaaacccaa gttatattag gagagattct gtaaactatt tcagtgacac tccaggagat 1020
ccgacaactc cagggtatcc ctccaaggat tccgacactg aacatatgtc accggtaggg 1080
agagtgccga ggataccatc ggtgccgatg agtgctagag atgtccaacc aattttagaa 1140
agattgaacg gcaggggttt tcaaattggg cccggtagta atataaaaga ttttggatca 1200
ttcactggac cttcaagctc tatcgataaa gtccatttgc ataatgagct aacttacaac 1260
atcaaggaaa tgagtggtgt agaagttagt atccctggta tattcactga gggggagatt 1320
attatcggag ctcataggga ttcgctcgcc tcgagtagcg ccggtgatgc aaatagtggc 1380

-continued

```
agcgctattc ttttagaaat tgcacgagga atgagtaaat tactgaagca tggttggaag   1440

ccactgcgtc ctatcaaact aataagttgg gatggtgaac gatccggcct tctgggatct   1500

acagattatg cagaagctca tgctgcgatt ctcaggagaa gggccttggt atacctaaat   1560

ctagataatg caatctctgg aacaaatttt cactgtaaag ccaacccact tttacaagac   1620

gtcatatacg aagctgctaa gctcacggaa tttaacgggc acgaagactg gtcattgttc   1680

gaccattgga aatacacttc taatgccact atttctctac ttgatgggct gtctagttac   1740

acttcatttc agtaccatct tggagtgccc gctgcacatt ttcagtttaa tgccaatgat   1800

acttcaggcg cagtctatca tagtaactcc gtattcgata gcccaacttg gttggaaaaa   1860

tttaccagtt ctgactacaa gttacacaac accatggcca tgtttgtagg tttgacaacg   1920

ctgatgctga gtgaaaacga actggcaaga ttcaatacac atgtttacct gaagaaaata   1980

tataactggt atatcgcatg gcactctaat ctatcttcag catttcccca ggacgatgaa   2040

gtgaacagct tagcaaaaag ggttctggac ttattaaaag ttgccacaca ggaagatagc   2100

atccaatttg accaacaaaa tgatattctc tataaagagt gtagggaagc tttacctgtt   2160

tgggcttttt acaaaaaaat caagagctat attaaactgc aacgatccaa tagcaaatca   2220

aagcaaattg atcaactatt tattacacac agaggactga aagacaggga atggatgaag   2280

tactctcttt tagcacctag taagtttgag ggatctgtcg gggaagtttt gcccggcctt   2340

cacgaaggat tggctgatat tgatagaaac gaggtcattc agtggttaac cattttgcta   2400

agccaattca gcaacgttcg ctatttactt caataa                             2436
```